(12) United States Patent
Hallam

(10) Patent No.: US 8,211,374 B2
(45) Date of Patent: Jul. 3, 2012

(54) AIR CLEANING DEVICE

(76) Inventor: David Richard Hallam, Denton (GB)

( * ) Notice: Subject to any disclaimer, the term of this patent is extended or adjusted under 35 U.S.C. 154(b) by 942 days.

(21) Appl. No.: 10/565,426

(22) PCT Filed: Jul. 19, 2004

(86) PCT No.: PCT/GB2004/003151
§ 371 (c)(1),
(2), (4) Date: Jan. 18, 2006

(87) PCT Pub. No.: WO2005/011846
PCT Pub. Date: Feb. 10, 2005

(65) Prior Publication Data
US 2006/0182672 A1 Aug. 17, 2006

Related U.S. Application Data

(60) Provisional application No. 60/577,952, filed on Jun. 8, 2004.

(30) Foreign Application Priority Data

Jul. 18, 2003 (GB) .................................. 0316837.4
Apr. 29, 2004 (GB) .................................. 0409547.7
May 13, 2004 (GB) .................................. 0410648.0

(51) Int. Cl.
*B01J 19/08* (2006.01)
*C01B 13/10* (2006.01)
(52) U.S. Cl. ............... 422/186.07; 204/176; 422/186.18
(58) Field of Classification Search ............. 422/186.07, 422/186.18; 204/176
See application file for complete search history.

(56) References Cited

U.S. PATENT DOCUMENTS

| 906,468 A | 12/1908 | Steynis |
| 1,157,859 A | 10/1915 | Freet |
| 1,454,219 A | 5/1923 | Goedicke |

(Continued)

FOREIGN PATENT DOCUMENTS

CA 1256284 6/1989

(Continued)

OTHER PUBLICATIONS

Masuda et al., "The Performance of an Integrated Air Purifier for Control of Aerosol, Microbial, and Odor" IEEE Transactions on Industry Applications 29 (4), pp. 774-780 (1993).*

(Continued)

*Primary Examiner* — Harry D Wilkins, III
*Assistant Examiner* — Bryan D. Ripa
(74) *Attorney, Agent, or Firm* — Young Basile Hanlon & MacFarlane PC

(57) ABSTRACT

The present invention provides an apparatus 1 for the treatment of air comprising a low power corona discharge ozone generator 5,6 inside a chamber 9 having an inlet 2 and an outlet 7, and at least one air flow impeller 3 for inducing a flow of air through the chamber 9. The ozone generator 5,6 is formed and arranged for generating a restricted concentration of ozone, within an inactivating zone 10 contained within the chamber 9, through which the air flow is passed. The restricted concentration is sufficient to inactivate airborne pollutant material entrained in the air flow, yet decays sufficiently outside the inactivating zone so that the concentration of ozone in the cleaned air expelled from the apparatus 1 is at a physiologically acceptable level without the use of an ozone decomposition catalyzer.

16 Claims, 3 Drawing Sheets

U.S. PATENT DOCUMENTS

| | | | |
|---|---|---|---|
| 1,505,669 A | 8/1924 | Quain | |
| 2,876,188 A | 3/1959 | Thorp et al. | |
| 2,937,983 A | 5/1960 | Ryan | |
| 3,256,164 A | 6/1966 | Donohue et al. | |
| 3,309,300 A | 3/1967 | Grosse et al. | |
| 3,326,747 A | 6/1967 | Ryan et al. | |
| 3,730,874 A | 5/1973 | Trüb | |
| 3,833,492 A | 9/1974 | Bollyky | 204/176 |
| 3,856,671 A | 12/1974 | Lee et al. | 210/63 |
| 3,865,733 A | 2/1975 | Taylor | 250/532 |
| 3,883,413 A | 5/1975 | Douglas-Hamilton | 204/176 |
| 3,892,237 A | 7/1975 | Steiner | 128/216 |
| 3,905,920 A | 9/1975 | Botcharoff | 250/536 |
| 3,921,002 A | 11/1975 | Williams et al. | 250/533 |
| 3,963,625 A | 6/1976 | Lowther | 250/533 |
| 3,967,131 A | 6/1976 | Slipiec et al. | 250/539 |
| 3,988,131 A | 10/1976 | Kanazawa et al. | 55/126 |
| 4,019,986 A | 4/1977 | Burris et al. | 210/139 |
| 4,025,441 A | 5/1977 | Tabata et al. | 250/540 |
| 4,035,657 A | 7/1977 | Carlson | 250/533 |
| 4,048,668 A | 9/1977 | Von Bargen et al. | 361/235 |
| 4,049,400 A * | 9/1977 | Bennett et al. | 96/80 |
| 4,049,552 A | 9/1977 | Arff | 210/192 |
| 4,051,045 A | 9/1977 | Yamamoto et al. | 250/536 |
| 4,062,748 A | 12/1977 | Imris | 204/176 |
| 4,079,260 A | 3/1978 | Dmitriev et al. | 250/540 |
| 4,095,115 A | 6/1978 | Orr, Jr. et al. | 250/538 |
| 4,101,783 A | 7/1978 | Hutter | 250/540 |
| 4,123,664 A | 10/1978 | Yamamura et al. | 250/536 |
| 4,124,467 A | 11/1978 | Pincon | 204/157.1 |
| 4,128,768 A | 12/1978 | Yamamoto et al. | 250/535 |
| 4,131,528 A | 12/1978 | Tsujimoto et al. | 204/157.1 |
| 4,140,608 A | 2/1979 | Vaseen | 204/176 |
| 4,159,971 A | 7/1979 | Gneupel | 250/540 |
| 4,167,466 A | 9/1979 | Orr, Jr. et al. | 204/176 |
| 4,167,484 A | 9/1979 | Morikawa | 250/533 |
| 4,182,663 A | 1/1980 | Vaseen | 204/157.1 |
| 4,187,615 A | 2/1980 | Iwata | 34/1 |
| 4,189,363 A | 2/1980 | Beitzel | 204/157.1 |
| 4,202,618 A | 5/1980 | Waschk et al. | 355/3 |
| 4,203,948 A | 5/1980 | Brundbjerg | 422/121 |
| 4,216,096 A | 8/1980 | Parè | 250/539 |
| 4,234,800 A | 11/1980 | Kenly, V et al. | 250/540 |
| 4,244,712 A | 1/1981 | Tongret | 55/124 |
| 4,252,623 A | 2/1981 | Vaseen | 204/157.1 |
| 4,316,782 A | 2/1982 | Foller et al. | 204/129 |
| 4,317,044 A | 2/1982 | Vaseen | 422/186.3 |
| 4,329,212 A | 5/1982 | Obenshain | 204/157.1 |
| 4,351,734 A | 9/1982 | Kauffman | 210/748 |
| 4,370,301 A | 1/1983 | Doi et al. | 422/122 |
| 4,375,395 A | 3/1983 | Foller et al. | 204/129 |
| 4,383,976 A | 5/1983 | Notaro | 422/186.18 |
| 4,386,055 A | 5/1983 | McBride | 422/186.18 |
| 4,411,756 A | 10/1983 | Bennett et al. | 204/176 |
| 4,416,747 A | 11/1983 | Menth et al. | 204/129 |
| 4,417,966 A | 11/1983 | Krauss et al. | 204/176 |
| 4,427,636 A | 1/1984 | Obenshain | 422/186.07 |
| 4,434,771 A | 3/1984 | Slomnicki | 123/539 |
| 4,461,744 A | 7/1984 | Erni et al. | 422/186.18 |
| 4,462,965 A | 7/1984 | Azuma et al. | 422/186.08 |
| 4,504,446 A | 3/1985 | Kunicki et al. | 422/186.19 |
| 4,541,989 A | 9/1985 | Foller | 422/186.07 |
| 4,555,335 A | 11/1985 | Burris | 210/192 |
| 4,614,573 A | 9/1986 | Masuda | 204/176 |
| 4,640,782 A | 2/1987 | Burleson | 210/748 |
| 4,650,573 A | 3/1987 | Nathanson | 210/136 |
| 4,656,010 A | 4/1987 | Leitzke et al. | 422/186.18 |
| 4,690,803 A | 9/1987 | Hirth | 422/186.18 |
| 4,696,800 A | 9/1987 | Sasaki et al. | 422/186.18 |
| 4,725,412 A | 2/1988 | Ito | 422/186.19 |
| 4,764,349 A | 8/1988 | Arff et al. | 422/186.18 |
| 4,786,489 A | 11/1988 | Grenier et al. | 423/581 |
| 4,790,980 A | 12/1988 | Erni et al. | 422/186.15 |
| 4,842,829 A | 6/1989 | Hirai et al. | 422/186.08 |
| 4,857,277 A | 8/1989 | Broomfield | 422/186.07 |
| 4,859,429 A | 8/1989 | Nisenson | 422/186.13 |
| 4,863,497 A | 9/1989 | Grenier et al. | 55/181 |
| 4,877,588 A | 10/1989 | Ditzler et al. | 422/186.19 |
| 4,886,645 A | 12/1989 | Fischer et al. | 422/186.18 |
| 4,904,289 A | 2/1990 | Miyakami et al. | 62/157 |
| 4,909,996 A | 3/1990 | Uys | 422/186.07 |
| 4,941,270 A | 7/1990 | Hoffman | 34/60 |
| 4,960,569 A * | 10/1990 | Fovell et al. | 422/186.19 |
| 4,976,920 A | 12/1990 | Jacob | 422/23 |
| 4,981,656 A | 1/1991 | Leitzke | 422/186.18 |
| 4,992,246 A | 2/1991 | Serizawa et al. | 422/186.13 |
| 5,004,587 A | 4/1991 | Tacchi | 422/186.19 |
| 5,008,087 A | 4/1991 | Batchelor | 422/186.22 |
| 5,015,442 A | 5/1991 | Hirai | 422/121 |
| 5,034,032 A | 7/1991 | Yikai et al. | 55/124 |
| 5,034,198 A | 7/1991 | Kaiga et al. | 422/186.07 |
| 5,039,314 A | 8/1991 | Lehner et al. | 55/26 |
| 5,047,127 A | 9/1991 | Tottori et al. | 204/176 |
| 5,055,115 A * | 10/1991 | Yikai et al. | 96/59 |
| 5,082,558 A | 1/1992 | Burris | 210/167 |
| 5,093,087 A | 3/1992 | Freeman | 422/186.15 |
| 5,120,512 A | 6/1992 | Masuda | 422/297 |
| 5,124,132 A | 6/1992 | Francis, Jr. et al. | 422/186.07 |
| 5,124,905 A | 6/1992 | Kniepkamp | 363/19 |
| 5,145,653 A | 9/1992 | Fischer et al. | 422/186.18 |
| 5,154,895 A | 10/1992 | Moon | 422/186.07 |
| 5,171,525 A | 12/1992 | Jacob | 562/392 |
| 5,185,903 A | 2/1993 | Choi | 15/339 |
| 5,186,903 A | 2/1993 | Cornwell | 422/122 |
| 5,203,972 A | 4/1993 | Shimamune et al. | 204/129 |
| 5,207,993 A | 5/1993 | Burris | 422/256 |
| 5,213,773 A | 5/1993 | Burris | 422/256 |
| 5,221,520 A | 6/1993 | Cornwell | 422/122 |
| 5,223,105 A | 6/1993 | Arthurson | 204/176 |
| 5,230,220 A | 7/1993 | Kang et al. | 62/78 |
| 5,268,151 A | 12/1993 | Reed et al. | 422/186.16 |
| 5,290,330 A * | 3/1994 | Tepper et al. | 96/381 |
| 5,302,343 A | 4/1994 | Jacob | 422/23 |
| 5,306,471 A | 4/1994 | Harbert et al. | 422/186.18 |
| 5,332,563 A | 7/1994 | Chang | 423/245 |
| 5,366,703 A | 11/1994 | Liechti et al. | 422/186.11 |
| 5,368,816 A | 11/1994 | Detzer | 422/28 |
| 5,387,400 A | 2/1995 | Pelster | 422/186.03 |
| 5,411,713 A | 5/1995 | Iwanaga | 422/186.15 |
| 5,445,798 A * | 8/1995 | Ikeda et al. | 422/121 |
| 5,460,705 A | 10/1995 | Murphy et al. | 204/252 |
| 5,466,425 A | 11/1995 | Adams | 422/186.3 |
| 5,478,533 A | 12/1995 | Inculet | 422/186.07 |
| 5,484,472 A | 1/1996 | Weinberg | 96/26 |
| 5,484,570 A | 1/1996 | Ikeda et al. | 422/1 |
| 5,493,754 A | 2/1996 | Gurstein et al. | 15/321 |
| 5,520,893 A | 5/1996 | Kasting, Jr. et al. | 422/305 |
| 5,527,459 A | 6/1996 | Ikeda et al. | 210/188 |
| 5,529,760 A | 6/1996 | Burris | 422/186.07 |
| 5,593,598 A | 1/1997 | McGinness et al. | 210/748 |
| 5,601,786 A | 2/1997 | Monagan | 422/108 |
| 5,611,868 A | 3/1997 | Gurstein et al. | 134/21 |
| 5,656,063 A | 8/1997 | Hsu | 95/58 |
| 5,656,242 A | 8/1997 | Morrow et al. | 422/121 |
| 5,667,564 A | 9/1997 | Weinberg | 96/58 |
| 5,681,533 A | 10/1997 | Hiromi | 422/121 |
| 5,702,507 A | 12/1997 | Wang | 96/55 |
| 5,752,878 A | 5/1998 | Balkany | 484/236 |
| 5,759,487 A | 6/1998 | Jung | 422/22 |
| 5,766,560 A | 6/1998 | Cole | 422/186.18 |
| 5,814,135 A | 9/1998 | Weinberg | 96/58 |
| 5,820,828 A | 10/1998 | Ferone | 422/124 |
| 5,824,274 A | 10/1998 | Long | 422/186.07 |
| 5,833,740 A | 11/1998 | Brais | 96/16 |
| 5,872,426 A | 2/1999 | Kunhardt et al. | 313/582 |
| 5,880,916 A | 3/1999 | Hsieh | 361/230 |
| 5,904,896 A | 5/1999 | High | 422/4 |
| 5,939,030 A | 8/1999 | Moxley et al. | 422/186.07 |
| 5,961,919 A | 10/1999 | Tachibana et al. | 422/3 |
| 5,972,196 A | 10/1999 | Murphy et al. | 205/466 |
| 6,005,349 A | 12/1999 | Kunhardt et al. | 315/111.21 |
| 6,013,021 A | 1/2000 | Lee | 600/9 |
| 6,013,189 A | 1/2000 | Burris | 210/750 |
| 6,039,884 A | 3/2000 | Burris et al. | 210/760 |
| 6,042,637 A | 3/2000 | Weinberg | 96/58 |
| 6,147,452 A | 11/2000 | Kunhardt et al. | 313/582 |
| 6,153,151 A | 11/2000 | Moxley et al. | 422/186.07 |

| | | | | |
|---|---|---|---|---|
| 6,200,539 B1 | 3/2001 | Sherman et al. | | 422/186.04 |
| 6,277,291 B1 | 8/2001 | Burris | | 210/760 |
| 6,342,187 B1 | 1/2002 | Jacob et al. | | 422/186.05 |
| 6,375,904 B1 | 4/2002 | Skillman et al. | | 422/172 |
| 6,387,241 B1 | 5/2002 | Murphy et al. | | 205/626 |
| 6,391,269 B1 | 5/2002 | Yoshimatu | | 422/186.07 |
| 6,447,731 B1 | 9/2002 | Sun et al. | | 422/121 |
| 6,468,953 B1 | 10/2002 | Hitchems et al. | | 510/218 |
| 6,475,215 B1 | 11/2002 | Tanrisever | | 606/45 |
| 6,503,458 B1 | 1/2003 | Ogle | | 422/121 |
| 6,508,982 B1 | 1/2003 | Shoji | | 422/22 |
| 6,545,608 B1 | 4/2003 | Kaufman | | 340/577 |
| RE38,130 E | 6/2003 | Adams | | 422/186.3 |
| 6,589,486 B1 | 7/2003 | Spanton | | 422/121 |
| 6,589,489 B2 | 7/2003 | Morrow et al. | | 422/186.3 |
| 6,673,137 B1 | 1/2004 | Wen | | 96/224 |
| 6,680,028 B1 | 1/2004 | Harris | | 422/122 |
| 2002/0039577 A1 | 4/2002 | Townsend et al. | | |
| 2002/0058000 A1 | 5/2002 | Smith | | |
| 2002/0094309 A1 | 7/2002 | Burris et al. | | |
| 2002/0098109 A1 | 7/2002 | Nelson et al. | | |
| 2002/0134736 A1 | 9/2002 | Burris et al. | | |
| 2003/0113246 A1 | 6/2003 | Saitou et al. | | |
| 2003/0146082 A1 | 8/2003 | Gibson et al. | | |
| 2003/0155228 A1* | 8/2003 | Mills et al. | | 204/157.3 |
| 2004/0047776 A1 | 3/2004 | Thomsen | | |
| 2004/0140194 A1* | 7/2004 | Taylor et al. | | 204/164 |
| 2004/0184972 A1* | 9/2004 | Kelly et al. | | 422/186.04 |

FOREIGN PATENT DOCUMENTS

| | | |
|---|---|---|
| CH | 669 116 A5 | 2/1989 |
| DE | 195 13 943 A1 | 10/1996 |
| DE | 298 08 126 U1 | 9/1998 |
| DE | 199 36 455 A1 | 2/2001 |
| DE | 199 42 839 A1 | 4/2001 |
| DE | 100 14 485 A1 | 9/2001 |
| EP | 0 731 320 A2 | 9/1996 |
| EP | 0 824 041 A2 | 2/1998 |
| EP | 1 079 183 A2 | 2/2001 |
| EP | 1 249 265 A1 | 10/2002 |
| EP | 1 348 448 A1 | 10/2003 |
| FR | 2 835 517 | 8/2003 |
| GB | 1 531 309 | 11/1978 |
| GB | 2 229 365 A | 3/1990 |
| GB | 2 340 035 A | 7/1998 |
| GB | 9916349.5 | 11/1999 |
| GB | 2 358 350 A | 7/2001 |
| GB | 2358350 A * | 7/2001 |
| JP | 62057662 A | 3/1987 |
| JP | 11-56673 | 6/1989 |
| JP | 03035018 A | 2/1991 |
| JP | 03207363 A | 9/1991 |
| JP | 05044958 A | 2/1993 |
| JP | 06105897 A | 4/1994 |
| JP | 07232028 A | 9/1995 |
| JP | 08114332 A | 5/1996 |
| JP | 08173517 A | 7/1996 |
| JP | 08253025 A | 10/1996 |
| JP | 09075436 A | 3/1997 |
| JP | 10253096 A | 9/1998 |
| JP | 200140688 A | 5/2000 |
| JP | 2000153178 A | 6/2000 |
| JP | 2001046906 | 2/2001 |
| JP | 1 175 943 | 1/2002 |
| JP | 2002276999 A | 9/2002 |
| SU | 19894708691 | 5/1998 |
| WO | WO 97/34682 | 9/1997 |
| WO | WO 00/01737 | 1/2000 |
| WO | 02/25180 A1 | 3/2002 |
| WO | WO 03/028773 A1 | 4/2003 |
| WO | WO 03028773 A1 * | 4/2003 |
| WO | WO 2004/047877 A2 | 6/2004 |

OTHER PUBLICATIONS

English abstract of JP 51103095A.*
Filtrete Filter MSDS.*
Rapid Communication article *Gas Phase Corona Discharges for Oxidation of Phenol in an Aqueous Solution*, by W.F.L.M. Hoeben, E. M. vanVeldhuizen, W. R. Rutgers and G. M. W. Kroesen, J. Phys. D: Appl. Phys 32 (1999) L133-L137.
*Cold Plasma Reactor with Dielectric Barrier Discharge*, printed by T. Opalinska, printed by Industrial Chemistry Research Institute, Rydygiera 8, 01 792 Warszawa, Poland.
*A Compact Corona Discharge Device (CDD™) for Non-Thermal Plasma Generation in Gasoline or Diesel Engine Exhaust*, Jack Ekchian, Vic Nowak, and Jim Rush, printed by Litex, Inc.
*Effects on Bacteria and Viruses*, written by Ozonet—Warren Wood, from website of Ozone Solutions, Inc.
*Make Some Ozone*, article taken from http://www.emanator.demon.co.uk/bigclive/ozone.html website.
*Honeywell Electronic Air Cleaners*, advertisement taken from http://www.hvacoracle.com/parts/ventilation/hw_eac.html website on Jul. 7, 2004.
QuickPure™ by Alab, LLC advertisement taken from http://www.quickpure.com/pg0.html website on Jun. 3, 2003.
ARIA PureAir Ltd. advertisement *Produce Comparisons*, taken from http://www.ariaair.com/comp.asp website on Feb. 7, 2003.
*Ozone Generators that are Sold as Air Cleaners: An Assessment of Effectiveness and Health Consequences, Indoor Air*—Publications article by U.S. Environmental Protection Agency.
*Investigation of gaseous ozone for MRSA decontamination of hospital side-rooms*, A. W. Berrington and S. J. Pedler, article by NCBI Pub Med 1: J Hosp Infect. Sep. 1998; 40(1):61-5; (National Library of Medicine "NLM") from NCBI website.
*Ozone Disinfection* Fact Sheet, by Clement Solomon, Peter Casey, Colleen Mackne, & Andrew Lake, project funded by the U.S. Environmental Protection Agency under Assistance Agreement No. CX824652; Technology Initiative (ETI), © 1998 by the National Small Flows Clearinghouse.
*Fundamentals of Ozonation* by Ron Brook and Ron Barnes (of Prozone Internation, Inc.), Home Vistek Commercial Ozone Systems.
Ozone Air disinfection and deodoursation advertisement for ozone generator taken from website http://www.1x1x1.com/ozone/air$_{13}$ disinfection.
*Biozone® Pure Wave™ versus Corona Discharge* article by Biozone Scientific advertisement from http://www.inspiredliving.com/cleanair/comoare_coronadischarge.html website.
*Overview of Ozone*, article from ARCE Systems, Inc. website: info@arcestems.com.
*Ozone Generation in Dry Air Using Pulsed Discharges with and without a Solid Dielectric Layer*, article by W. J. M. Samaranayake, YT. Miyahara, T. Namihira, S. Katsuki, R. Hackam, H. Akiyama, published: IEEE Trans. DEI, vol. 87 pp. 687-697, 2001.
*Corona Discharge Treatment for Medical Surface Preparation*, by Bruce Stobbe, article from Medical Device & Diagnostic Industry Magazine, originally published Feb. 2000, from website: http://www.devicelink.com/mddi/archive/00/02/004.html.
*A Simple and Efficient Ozone, Generator* by Debra J. Sponholtz, Michael A. Walters, Jimmy Tung, and Joseph J. BelBruno, *Journal of Chemical Education*, vol. 76, No. 12, Dec. 1999, Department of Chemistry, Dartmouth College, Hanover, NH 03755.
*A History of Patented Methods of Ozone Production From 1897 to 1997*, IAngela E. Miller, Wm. R. Grow, Leigh Ann Dees, Michael R. Mitchell, Thomas J. Manning, Laboratory of Physical Environmental Sciences Department of Chemistry, Valdosta State University, Valdosta, GA 31698.
*Electrical Discharges (How the spark, glow and arc work)*, article composed by J. B. Calvert, Nov. 3, 2002, on website http://www.du.edu/~icalvert/phys/dischg.html.
*The Fontan Device*, article taken from website http://cloudbase.phy.umist.ac.uk/people/dorsey/Font.html on Jul. 3, 2003
*5.2 Ozonolysis of Alkenes under Atmospheric Conditions*, article taken from website http://www.physchem.uni-suppertal.de/P.../05_2_Ozonolysis/05_2_1_Peroxides.html on Jul. 3, 2003.
*3. Ozone*, EPA Guidance Manual, "Alternative Disinfectants and Oxidants", Apr. 1999.

*Ozone Out for Indoor Air Cleaners*, by John Manuel, from "Home Energy Magazine Online" Nov./Dec. 1998, from website http://hem.dis.anl.gov/eehem/98/981110.htrl.

*The Technical Merits and Application of Different Types of Air Cleaning Technology*, by Stephen H. Zitin of Bioclimatic, Inc., May 13, 2003, from website: http://www.wescorhvac.com/BioPaper.html.

*Frequently Asked Questions About our IG-133-model series ionizers*, from advertisement of copyright © 2004 Comtech Research LLC, Dec. 16, 2004.

*The Low Voltage Ozone Generator*, Sergey I. Andreev, by Ohio Scientific Consulting Corporation, (OSCC).

* cited by examiner

AIR CLEANING DEVICE

FIELD OF THE INVENTION

The present invention relates to an apparatus and method for the removal of airborne pollutants or impurities such as micro-organisms, smoke particles or odours from air by means of transient treatment of the air in a low power corona discharge field.

BACKGROUND OF THE INVENTION

The use of ozone in many applications involving sterilising and cleaning air is well known. Ozone generating devices have been designed for a great variety of domestic and industrial applications. All depend on ozone's great oxidising potential to kill micro-organisms and oxidise other organic particles and materials. Depending on the application, ozone is generated by means of ultraviolet radiation or electrical discharge to convert atmospheric oxygen to triatomic ozone, which can be highly effective at destroying organic atmospheric contaminants. Ozone is, however, highly toxic at high concentrations and it is increasingly clear that even at much lower concentrations it is irritant, being particularly linked with asthmatic complaints in those chronically exposed to it. In many territories there are strict statutory limits on the concentration of ozone to which members of the public and employees at a place of work may be exposed. In the UK, the Health and Safety Executive recommendation (EH38) is that the exposure limit to ozone should be 0.1 ppm (0.2 mg m-3) as an 8-hour time-weighted average concentration, with a short-term exposure limit of 0.3 ppm (0.6 mg m-3) as a 15-minute time-weighted average concentration.

Although undoubtedly effective at high concentrations, there is considerable evidence that ozone is ineffective as a biocide or in oxidising organic contaminants at concentrations that are safe for chronic human exposure (Dyas et al, 1983, J Clin Pathol 36: 1102-1104; Berrington and Pedlar, 1998, J Hosp Infect 40: 61-65; Esswein et al, 1994, Appl Occup Environ Hygiene 9: 139-146). Such effect as it has in reducing odours is, in many cases, probably a mere masking with its own characteristic smell.

Alternative approaches to removing micro-organisms and other small airborne organic particles, such as smoke, obviously include direct filtration of the air. Various type of filter including so-called High Efficiency Particulate Air (HEPA) filters (defined as removing 99.97% of particles of 0.3 micron size) and electrostatic HAF (High Airflow, electret) filters capable of similar performance at higher airflows are commonly used. Although effective in some situations, such filters suffer from the disadvantages that trapped (and potentially infective) material remains on the filters, necessitating frequent changes of filter and remaining a hazard until the filters are replaced. This is a particular problem where the air being filtered is humid. In addition, such filters are incapable of removing small viral particles.

In my earlier GB 2358350 there is disclosed a proposed hand drier apparatus using a corona unit with quartz glass and stainless steel mesh electrodes and operating at 9 mA and 4 kv in order to eject a stream of ozone at the user. Further research has disclosed, however, that the proposal as disclosed in this publication would be quite impractical—quite apart from exposing the user to dangerous levels of ozone.

Thus there remains a need for an efficient means of inactivating airborne pollutants such as organic particles, micro-organisms and odours in air without release of potentially hazardous levels of ozone into an enclosed environment.

SUMMARY OF THE INVENTION

The current invention concerns a method of using a low power corona discharge field to effectively sterilise air of micro-organisms or oxidise organic airborne contaminants and particles in such a way that the air is only transiently exposed to high concentrations of ozone and is returned to the environment with the level of ozone reduced to acceptable levels for safe exposure of those living or working in the immediate environment. Preferably the concentration of ozone expelled from the apparatus is less than 0.3 ppm. Preferably, it is less than 0.2 ppm and more preferably less than 0.1 ppm.

It has now been found that it is possible, using a low power coronal discharge ozone generator unit, to generate restricted ozone concentrations within an inactivating zone in close proximity to the unit and contained within the apparatus housing, which are sufficient to inactivate a wide range of airborne pollutants in an airflow passing through said zone, yet which reduce to safe levels sufficiently rapidly that the treated air issuing from the apparatus has physiologically acceptable ozone concentrations without the need for special catalyzers. Extensive experimental work (discussed in detail hereinbelow), has shown that even with ozone concentrations up to 100 ppm in the inactivation zone, exit concentrations of less than 0.1 ppm are achieved.

Thus in one aspect the present invention provides an apparatus for the treatment of air comprising a low power corona discharge ozone generator mounted inside a chamber having an air inlet and an air outlet and at least one air flow impeller formed and arranged for inducing a flow of air through said chamber, said ozone generator being formed and arranged for generating a restricted concentration of ozone and any other reactive species formed together therewith, within an inactivating zone contained within said chamber, through which said air flow is passed in use of said apparatus, which restricted concentration is sufficient effectively to inactivate airborne pollutant material entrained in said air flow, yet which restricted concentration decays sufficiently outside said inactivating zone so that the concentration of ozone in the cleaned air expelled from said apparatus is at a physiologically acceptable level without the use of an ozone decomposition catalyzer.

As used herein the expression "inactivating zone" means a restricted volume surrounding the low power corona discharge ozone generator containing an elevated concentration of ozone (and any other reactive species may be generated together with the ozone by the low power coronal discharge ozone generator), sufficient to substantially inactivate airborne pollutants.

In accordance with the present invention the low power coronal discharge ozone generator is formed and arranged so that the inactivating zone is contained within a chamber i.e. does not extend outside of the confines of the chamber. The chamber is generally in the form of a box, cabinet or casing, or the like. The chamber is provided with (at least one) inlet and (at least one) outlet, of any convenient form, for example a conduit or simply one or more apertures capable of passing a through flow of air that is produced by at least one air flow impeller, most conveniently an electrically-driven fan so arranged as to efficiently draw air in through the inlets, through the inactivating zone of the apparatus and out though the outlets. More particularly the air flow impeller is formed and arranged to provide a flow of air through the chamber resulting in a generally turbulent flow through the chamber and the inactivating zone. In practice 1 have found that a suitable air flow can be obtained with a fan, mounted in a simple generally box-shaped chamber with a non-rectilinear route between the inlet, impeller, and outlet, and running at a relatively wide range of flow rates. With an apparatus having a chamber volume in the order of 0.1 to 0.3 m3, 1 have found that hourly flow rates of the order of from 50 to 750 m3h-1, preferably 50 to 500 m3h-1, most preferably 150 to 500 m3h-1, can provide substantially complete inactivation in a single pass—at least at typical pollutant loading levels in enclosed working, residential, transportation, recreational and like environments, whilst restricting ozone emissions to physiologically acceptable levels. Naturally higher than average pollutant loadings and/or more resistant pollutants, may require somewhat lower maximum air flow rates and/or multiple passes through the apparatus, than are required for other cases.

Similarly I have found that effective inactivation and ozone containment within the apparatus, may be achieved with a relatively wide range of residence times of the airflow within the chamber of the apparatus. Preferably there is used a residence time in the range from 0.2 to 20 seconds, preferably from 0.3 to 15 seconds, advantageously from 0.5 to 10 seconds.

Various forms of impeller may be used. Conveniently there is used an electric fan running at a speed of the order of 2000 to 4000 rpm. A range of different flow rates may conveniently be obtained for a given fan speed by simply changing the fan blade angle.

In addition to the particular benefit of providing a rapidly decaying restricted concentration ozone supply, such low power coronal discharge ozone generators also have significant safety benefits in the case of any possible apparatus malfunctions, maintenance operations etc. Power to provide a suitable ozone-generating corona discharge is suitably provided by a transformer providing a high-voltage alternating current. It will be appreciated that the voltage and current parameters of the unit required to achieve a corona discharge will depend principally on the nature of the dielectric used, as further discussed hereinbelow. In general though I have found that operating voltages below 1 kV are not practical, and preferably there is used an operating voltage in the range from 1 to 6 kV, most desirably from 3 to 5 kV, for example about 4 kV. It will be appreciated that the current required to maintain the corona discharge is significantly less than that required to initiate it. The current (and hence power) of coronal discharge ozone generator units is normally expressed in terms of the starting current. In general I have found that there should be used a (starting) current in the range from 1 to 10 mA, preferably at least 3 mA. The power of the unit will of course depend on the voltage and current combination. Restriction of the power of the unit helps to ensure that the inactivation field is contained within the chamber. In this connection it will be appreciated that a somewhat higher power unit might, in principle, be used with a larger chamber. The power should generally be not more than 50 watts, and is preferably at least 4 watts. Typically the power is in the range from 10 to 40 watts. These power levels have in particular been found to be convenient with a unit having a chamber volume of the order of 0.02 to 1.0 m3. (It will be appreciated that on the one hand the chamber should not be smaller than a volume required to contain said inactivation zone of the ozone generator(s), and on the other hand not so large that substantially the whole of the airflow does not pass through said inactivation zone in the course of its transit through the chamber.)

Even with such low power corona discharge devices it has been found possible to achieve well contained localized highly inactivating concentrations of ozone sufficient to inactivate a very wide range of airborne pollutants.

Advantageously there is used a transformer provided with an anti-surge and/or anti-spike device(s), in order to minimize transient excursions of the output voltage above the normal level which could result in temporary extension of the inactivation zone outside of the chamber and/or generation of excessively high ozone levels.

Desirably also there is used a transformer which is "potted" or encased in a suitable insulating material in order to minimize the risk of possible breakdown in the course of use of the apparatus of the invention.

A wide range of frequencies may be used in the AC supply to the low power corona discharge device, and indeed somewhat higher frequencies may safely be used than is possible with conventional high power ozone generators. Conveniently there may be used an AC supply with a frequency in the range from 50 to 1000 Hz.

Various forms of low power corona discharge device are known in the art. In accordance with the present invention there is desirably used one with a solid dielectric in order to obtain a more consistent and reliable ozone generation performance. Various geometries are also possible. Thus, for example, there may be used a substantially planar unit with a flat dielectric plate with electrodes on opposite sides thereof. More preferably there is used a generally tubular geometry, with a tubular dielectric with generally tubular electrodes on the inner and outer faces thereof. It will be appreciated that ozone will be generated at both electrodes. Preferably there is used a generally mesh form electrode in order to maximize the areas of dielectric surface at which ozone is generated. In this connection it will be appreciated that substantially "closed" meshes are less desirable as these reduce the exposed dielectric surface. On the other hand excessively "open" meshes are generally less efficient in the amount of ozone generated for a give size of unit.

In a highly preferred embodiment, the low power corona discharge ozone generator comprises tubular stainless steel gauze electrodes separated by a silica glass dielectric. (Whilst various other suitable electrode materials are known in the art, stainless steel is particularly convenient due to inter alia its resistance to corrosion and to oxidative and other damage from the corona discharge.) The purpose of gauze electrodes is to maximize the surface available for the corona discharge and hence generation of ozone and other reactive species. However, other factors, such as the effects on the electromagnetic field generated, particularly hysteresis effects relating to the generation and collapse of the field during the 50 Hz cycle of the alternating current, also influence the choice of gauze and the fineness of the mesh. In a preferred embodiment the gauze on the outer electrode is coarser than that of the inner electrode as this favours the production of ozone on the outer, rather than inner, electrode. In a more preferred embodiment, the mesh count of the inner electrode is from 50 to 30×45 to 25 (per inch or 25.4 mm) and that of the outer electrode is 35 to 20×40 to 20. In a particularly favoured embodiment, the mesh count of the inner electrode is 40×34 (per inch or 25.4 mm) using a 38 swg wire (0.15 mm diameter) and that of the outer electrode is 24×28 using a 30 swg wire (0.3 mm diameter).

It is also desirable for effective corona discharge to take place that the mass of the electrodes be substantially balanced, i.e. to differ by not more than 20%, preferably not more than 10%. This is especially significant in the case of annular configuration corona discharge devices of the kind described elsewhere herein.

It will also be appreciated that the power of the corona discharge ozone generator is related to the size of the electrodes. In general it is preferred that each of the mesh electrodes should have an area in the range from 25 to 100 cm2, preferably from 40 to 90 cm2.

It will be appreciated that with a solid dielectric, the generation of a corona discharge is very much dependent on the thickness of the dielectric, and especially at lower voltages, as used in accordance with the present invention, it is necessary to minimize the thickness of the dielectric. It will also be understood, though, that the dielectric must be strong enough to avoid damage by the substantial stresses encountered inside a corona discharge. In this connection I have found that conventional glasses when used at thicknesses low enough for corona discharge to occur at voltages used in accordance with the present invention are highly susceptible to shattering, and it is necessary to use suitably strengthened glasses. Suitable glasses include borosilicate glass, especially borosilicate glass strengthened with titanium dioxide. Preferably there is used a glass dielectric having a wall thickness of from approximately 0.70 mm to 1.75 mm, and more preferably from 0.8 to 1.1 mm, in order to withstand the stresses of the discharges and to have suitable dielectric qualities to allow a corona discharge to take place. It is also advantageous if the glass is a high quality quartz silicate or borosilicate with added titanium dioxide.

Ozone generation occurs during the negative half cycle of the alternating current, at each electrode in turn. During the corresponding positive half cycle there is a tendency for resident ozone to be broken down, but this is a slower process than generation, and in any case the flow of air removes ozone from the corona discharge area as it is formed. This leads to a net production of ozone. The electrochemistry of such methods of ozone production is known in the art.

Ozone thus generated spontaneously breaks down. The half-life in air is dependent on a variety of factors including temperature and concentration but is generally at least several minutes or hours. However, this half-life is generally significantly shortened by humidity and by the presence of oxidisable substrates, solid surfaces and specific catalysts. The generation of ozone in accordance with the present invention in a restricted inactivation zone around a low power corona discharge ozone generator unit, in such a way that it rapidly decomposes to a physiologically acceptable level outside the zone, which obviates the need for the use of special catalysts, is conveniently referred to by the applicant as "closed coupled-field" generation technology.

It should be noted that, although corona discharge is a convenient method of generating ozone, a number of other highly reactive oxygen and nitrogen species may also be generated in air alongside the ozone. The presence of these excited molecules and the generation of further reactive products by their inter-reactions can further contribute to the inactivating activity in the inactivation zone surrounding the alternating current corona discharge tube of the invention.

The inactivating effect of the apparatus of the invention may be used for inactivating a wide range of pollutants, including inter alia microbiological pollutants such as airborne bacteria, viruses and fungal spores, smoke, and various volatile organic compounds, in a wide range of situations so as to improve the quality of the air.

Situations in which the anti-microbial applications of the invention are especially useful include hospitals, food preparation areas, laboratories and locations with limited ventilation, where air may be re-circulated. Storage of sterile instruments and materials in an atmosphere sterilised by means of the invention may extend their shelf life, with considerable consequent savings. The invention provides a means of supplying a unit for such storage with sterile, dry air capable of maintaining the sterility of stored instruments for extended periods. One particularly useful application is in flood-damaged buildings, where removal of fungal spores from the air can minimize subsequent growth of mould and development of rot in the fabric of the building, with significant reduction in damage and costs of repair. In another application, the apparatus may be installed in ducting or pipework carrying a flow of air, such as may for example be used in an air-conditioning system.

In situations where the main use of the apparatus is the removal of smoke particles, it is preferred that the burden of oily and tarry particulates especially particles passing into the inactivation zone is reduced by the presence of a pre-filter upstream of the inactivation zone, conveniently at the inlet to the chamber of the apparatus. Various filters suitable for trapping such pollutants are well known in the art. Where the apparatus is used to remove micro-organisms from air that is largely free of high levels of other contaminants, the preferred configuration is the provision of a post-filter on the outlet of the apparatus. Naturally there may be used both pre- and post-filtration together, and in one convenient form of apparatus of the invention the inlet and outlet means are disposed in proximity to each other and the apparatus provided with a single filter mounting so that respective portions of the filter occlude respective ones of the inlet and outlet means thereby simplifying maintenance and filter replacement.

Electrostatic filters are particularly preferred and are well-known in the art. In principle, they use charged filter media to trap charged particles. Most small units are passive in that they use the friction due to the passage of air through the filter to generate a static charge on specialised materials, which is the principle of the well-known HEPA filters. More recently, permanently polarised 'electret' filter media with particularly high electrostatic charge surfaces, as described in (Myers & Arnold, Winter 2003, International Nonwovens Journal and International patent application publication WO 00/01737), have formed the basis of so-called HAF (High Air-Flow) filters, which have far greater face speeds whilst maintaining highly efficient filtering of very small particles (down to 0.1□). Large industrial electrostatic precipitators (or 'electronic' filters) use charged plates or a corona discharge to actively impart charge to airborne particles. As used herein, 'electrostatic filters' includes all of these types.

Without being bound by any particular theory or model, it is possible that the combination of the ozone generating low power corona discharge ozone generator unit of the invention, combined with an electrostatic post-filter, may provide a particular synergistic benefit with the filter materials, which in some way increases the electrostatic attraction between the airborne particulates emerging from the inactivation zone and the filter surfaces, which results in a significant reduction in the size of the particles which may be trapped by the electrostatic filter used in preferred forms of apparatus of the invention, which has been found by the inventor. This is particularly significant in relation to viruses as these generally have a size of the order of 0.1 micron, which is below the normal minimum particle size of 0.3 microns which can be trapped by HAF filters. Examination of HAF filters used in apparatus of the present invention indicates though that even such viral particles can be successfully trapped, as well as being inactivated.

Thus in a further aspect the present invention provides an apparatus for the cleaning of air comprising; a means of generating and retaining ozone and other reactive species within a confined field and a means of drawing a flow of air through said field, wherein said field comprises a concentration of ozone and/or other reactive species sufficient to effectively oxidise airborne organic material but wherein the concentration of ozone in the cleaned air expelled from said apparatus is within safe limits for a confined environment.

In accordance with the present invention the concentration of ozone in the air expelled from the apparatus is at a physiologically acceptable level. In practice different countries have slightly higher or lower standards for what are considered to be acceptable levels. In general it is preferred that the air expelled from the apparatus should have an ozone concentration of less than 0.3 ppm at 1 meter from the apparatus air exhaust outlet, more preferably less than 0.2 ppm, most preferably less than 0.1 ppm. Desirably the ozone concentrations are less than these values at the exhaust outlet. An important consideration is the accumulation of ozone in the area surrounding the apparatus during operation. Preferably the concentration of ozone at 1 meter from the apparatus after 15 minutes of operation is less than 0.3 ppm, more preferably less than 0.2 ppm, most preferably less than 0.1 ppm.

The chamber of the apparatus is generally defined by a casing which may be of any convenient material. Advantageously the casing is comprised of metal, for example steel or aluminium, or a plastics material (or GRP) impregnated and/or coated with metallic material, suitable to suppress radio frequency interference resulting from the corona discharge and is suitably earthed.

In another aspect, the invention provides a method of cleaning air comprising generating and retaining ozone and other reactive species within a confined field, wherein said field comprises a concentration of ozone or other reactive species sufficient to effectively oxidise airborne organic material and drawing a flow of air through said field, such that the cleaned air having passed through said field contains a concentration of ozone that is within safe limits for a confined environment, preferably less than 0.3 ppm, more preferably 0.2 ppm, most preferably 0.1 ppm.

It will be appreciated that a particular benefit of the invention is in increasing the usefulness of filters, particularly filters designed to remove airborne micro-organisms. In many conventional air filters wherein micro-organisms which have not previously been inactivated, are trapped, these tend to multiply more or less rapidly thereby presenting a hazard in handling of the filter when it is replaced, and increasing the risk of release of active micro-organisms back into the airflow emerging from the filter. With the apparatus of the present invention, however, the micro-organisms are substantially inactivated prior to being trapped by the filter, thereby avoiding the above disadvantages. Any which have been trapped without having been fully inactivated, may moreover be subjected to further inactivation treatment by any residual ozone passing into the filter. In this way, the combination of highly efficient filters, such as HEPA or HAF electrostatic filters capable of effectively removing particles as small as 0.1 to 0.3 microns, may provide a further synergistic effect, with an increased benefit over that obtained over either alone, in terms of prolonged efficient filtering and killing of potentially infective micro-organisms.

Another particularly preferred application of the apparatus of the invention is one wherein air is cleaned of smoke particles. In this case the inlet(s) is fitted with one or more filters. Preferably, the filter assembly comprises two or more filter elements, more preferably, at least one of the elements is an electrostatic filter. In the case of applications where the smoke comprises tobacco smoke, there is advantageously used a filter element which traps oil and/or tar materials found in such smoke.

In another aspect the present invention provides a method of cleaning air comprising the steps of:
providing an apparatus according to the present invention;
powering the ozone generator of said apparatus so as to generate ozone in the inactivation zone of said apparatus; and operating said airflow impeller so as to pass a flow of said air through said inactivation zone.

Also provided is method of cleaning air comprising generating and retaining ozone within a confined field, wherein said field comprises a concentration of ozone or other reactive species sufficient to effectively oxidise airborne organic material and drawing a flow of air through said field, such that the cleaned air having passed through said field contains a concentration of ozone that is within safe limits for a confined environment, preferably less than 0.3 ppm ozone, more preferably less than 0.2 ppm, most preferably 0.1 ppm, wherein air is cleared of smoke particles and wherein air passes through a filter before exposure to ozone.

It will be appreciated that in general where airborne pollutants are being removed from a room or other more or less enclosed space, the amount of treatment required will depend on the nature of the pollutant, and possibly also the burden or loading thereof in the air. Whilst there may in principle be used multiple passes to progressively reduce the pollutant loading, it is a particular advantage of the invention that the relatively high ozone concentrations which can be achieved with apparatus of the invention within the restricted contained inactivation zone, can usually provide substantially complete inactivation within a single pass, thereby minimizing the number of air changes required. Typically where it is desired to remove bacterial pollutants there should be provided at least 5 air changes per hour, whilst in the case of locations with moderate to high tobacco smoke loadings, it may be desirable to provide at least 10 or more air changes. The total airflow required to treat a room may be readily determined from the volume of the room and the number of air changes required. Whilst it might in principle be possible to achieve higher flow rates with larger sizes of apparatus, it is generally preferred to achieve them by using multiple apparatus units. In this connection it will be appreciated that more than one corona discharge ozone generator may be mounted in the same chamber, provided the inactivation zones of all the generators are contained within the chamber. Furthermore, more than one corona discharge device may be powered by one (common) transformer, albeit the total power of the transformer will then be divided between the corona discharge devices.

DETAILED DESCRIPTION OF THE INVENTION

Further preferred features and advantages of the invention will appear from the following detailed examples and description given by way of example with reference to the accompanying drawings in which.

Figure 1:
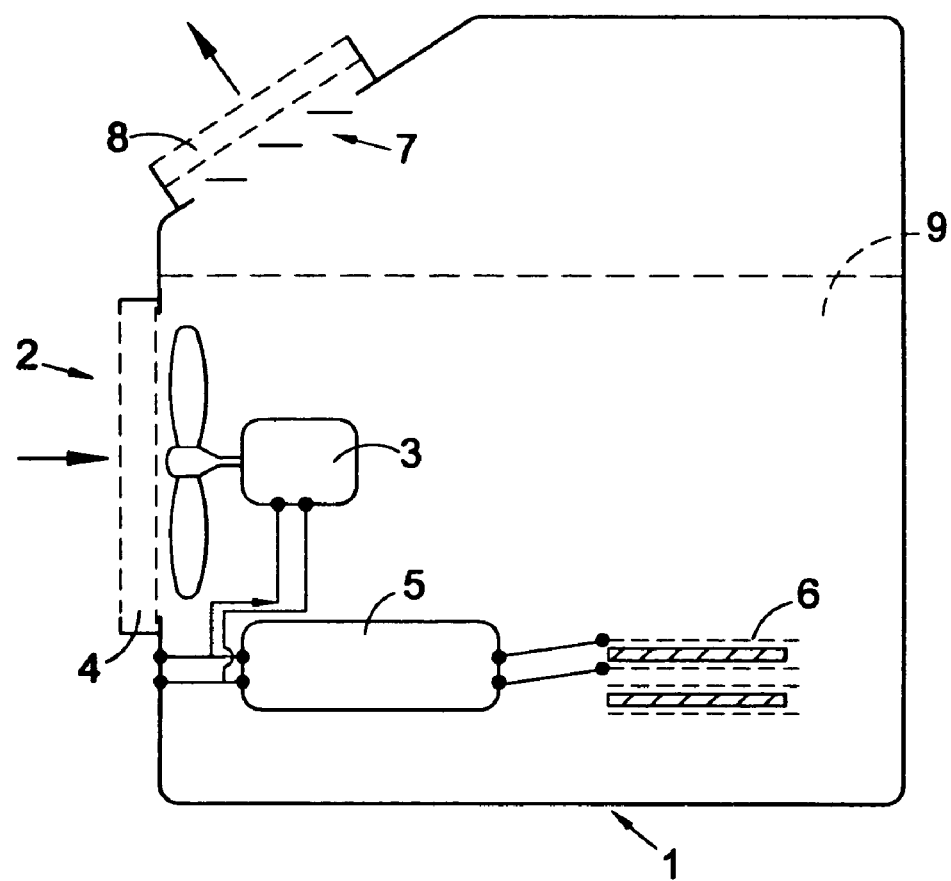
FIG. 1 shows a schematic cross-section of a first embodiment of an air treatment apparatus of the invention suitable for the removal of micro-organisms from air.

FIG. 1 shows a schematic cross-section of an apparatus for the removal of micro-organisms from air according to the invention. 1 indicates the casing, 2 the inlet, 3 the fan, 4 an optional pre-filter, 5 the transformer, 6 the corona discharge ozone generator unit, 7 the outlet, and 8 the electrostatic post-filter. An inactivation zone 9 (indicated schematically) extends around the ozone generator unit 6.

Figure 2:
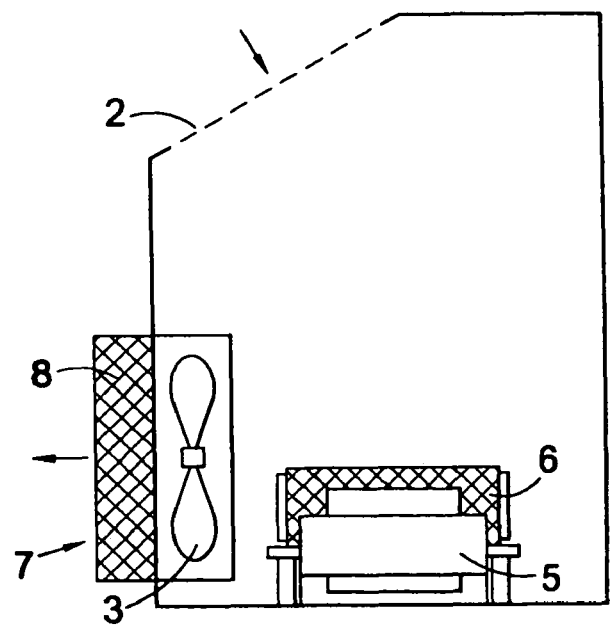
FIG. 2 is a sectional elevation of a further embodiment illustrating a practical arrangement of the low power coronal discharge ozone generator therein.
Figure 3:
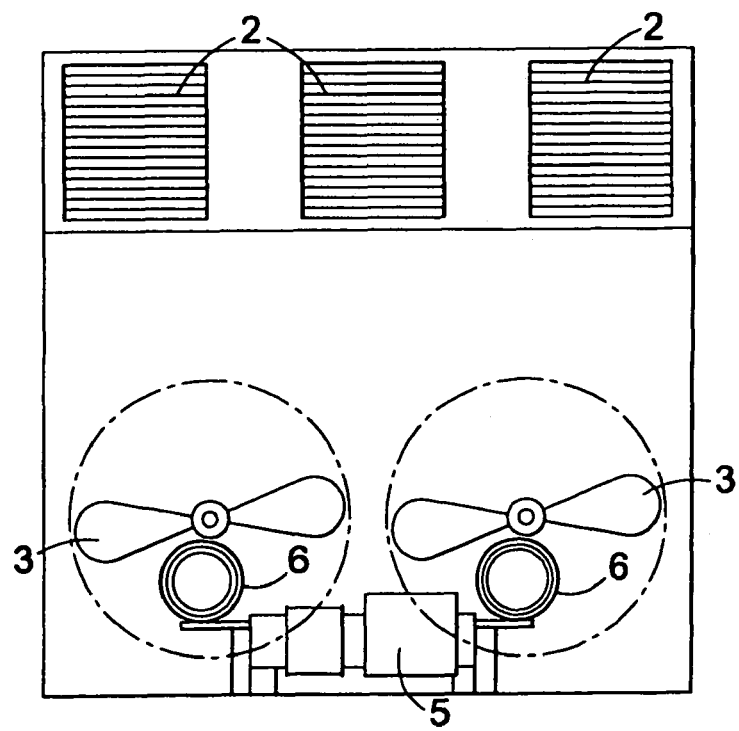
FIG. 3 is a front elevation of the embodiment of FIG. 2.

FIGS. 2 and 3 show a practical arrangement of two ozone generator units 6 powered by a single common transformer unit 5. In this case the direction of fan rotation is reversed with respect to that of the embodiment of FIG. 1 so that the upper openings serve as the inlets 2, and the openings adjacent the two fans 3 serve as the outlets 7.

Figure 4:
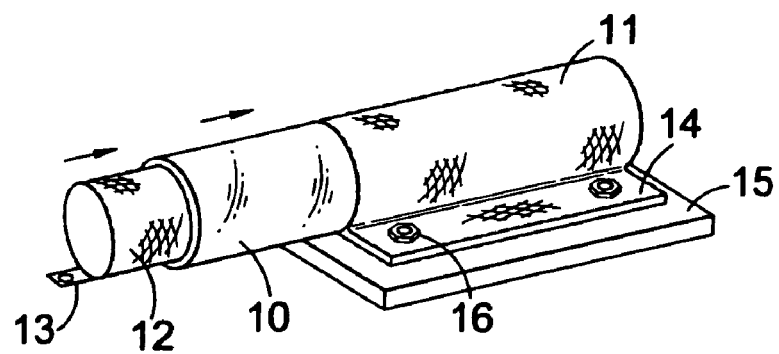
FIG. 4 is a partly exploded perspective view the construction of the corona discharge device of the corona discharge ozone generator of the apparatus of FIG. 1.

FIG. 4 is a partly exploded view showing the construction of the corona discharge ozone-generating unit 6. 10 is the glass tube dielectric, 11 the outer mesh electrode, 12 the inner mesh electrode fitted with a spade end electrical connector 13. When constructed the outer mesh 12 is rolled into a tube with a flange 14 providing a fixing means. 15 is an insulating plastic plate for mounting the assembly by means of insulating screws, nuts and washers 16.

Figure 5:
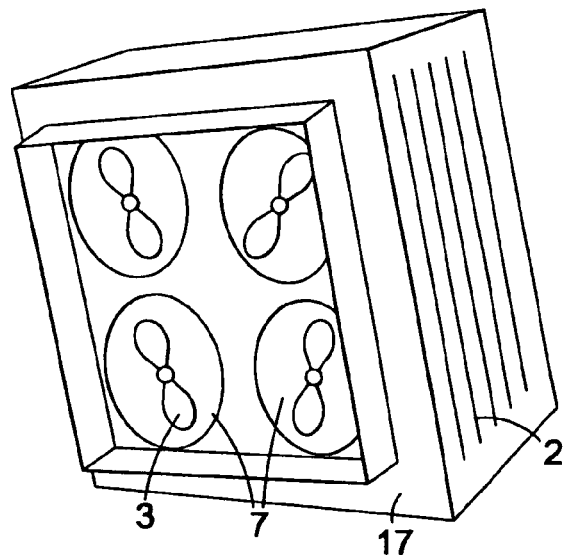
FIG. 5 shows a general perspective view of another embodiment of the invention.

FIG. 5 shows a perspective view of one embodiment of the invention showing a casing 17 for a model with four outlet apertures 7 for respective fans 3.

Figure 6:
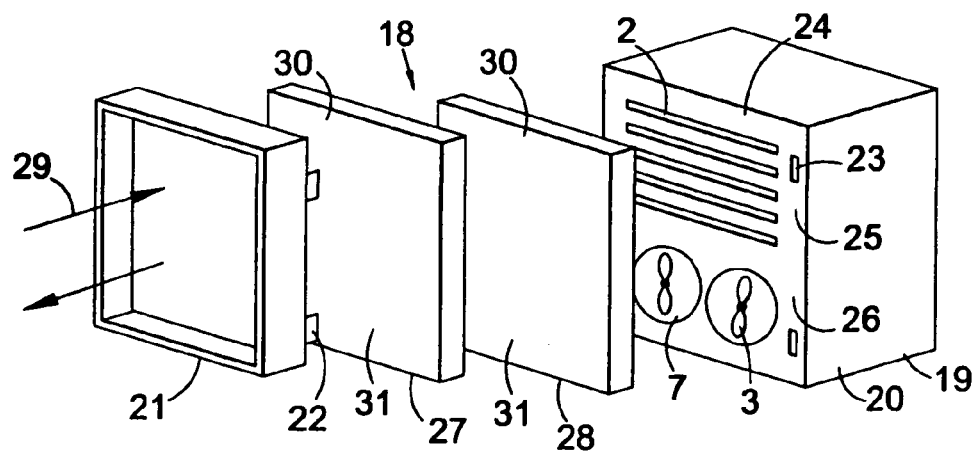
FIG. 6 is an exploded perspective view illustrating the use of a single filter assembly for pre- and post-filtering.

FIG. 6 illustrates the use of a single common filter assembly 18 in a two-fan device 19 to provide both pre- and post-filtering. This configuration is especially useful for removal of smoke. The unit comprises a force chamber partially contained by casing 20, fitted with a filter holder 21 provided with lugs 22 for snap-fit interengagement with mounting points 23 on the front face 24 of the casing 20. The inlets 2 and outlets 7 are disposed in upper and lower portions 25, 26, respectively, of the front face 24.

The filter holder 21 supports the filter assembly 18 across both the upper and lower portions 25,26 of the front face 24. In this example there is provided an external filter 27 which is a 3M low pressure 3202WAT Filtrete™ tobacco smoke filter. Inside this is a second filter 28, in this case a 3M Filtrete™ HAF filter. The force chamber 20 contains two fans 3, which draw air 29 into the unit 20. As a result, the smoke laden air is first drawn through the upper area 30 of the two filter layers 27,28 into the unit 20, passes through the low power corona discharge field (not shown) and then exits through a lower area 31 of the two filter layers 27,28.

EXAMPLE 1

Apparatus for the Removal of Micro-Organisms from Air Construction

With reference to FIG. 1, the apparatus comprises a containment means consisting of a casing (1), in this case of thin sheet metal construction. This casing has an inlet (2) fitted with an electrically-driven fan (3) so positioned as to produce an efficient flow of air into the apparatus. The inlet may, optionally, have a pre-filter (4) fitted. Within the casing is an approximately 4 W corona discharge unit (6) operating at approximately 4 kV and 1 mA. A transformer (5) supplies power to the corona discharge unit. In this case the outlet (7) is fitted with an electrostatic post-filter (8, HAF, Filtrete™ 3M Corporation)

The details of the construction of the corona discharge unit are shown in FIG. 4. A silica glass tube dielectric (10) with a wall thickness of 0.8-1.1 mm has outer (11) and inner (12) essentially tubular stainless steel gauze electrodes. The dimensions are not critical but in this case the glass tube is approximately 63 mm long, inner electrode is formed from a 40×34 mesh number gauze of approximately 71×63 mm, and the outer electrode is formed from a coarser 24×28 mesh number gauze of approximately 133×63 mm. The inner electrode fits within the glass tube and is fitted with a spade end electrical connector (13). The outer electrode is formed into a cylinder fitting around the glass tube with a flange (14) allowing it to be fixed, together with the glass tube and inner electrode assembly, to a suitable insulating plastic base plate (15) by means of insulating nylon screws and washers and nuts (16).

FIG. 5 shows a casing suitable for use as a containment means, as described above. By configuring fans appropriately, air may by drawn in through the louvred apertures and out through the circular apertures, optionally through a post-filter. This arrangement is particularly suitable for use in an apparatus for the removal of micro-organisms from air.

Performance

This unit has been tested for efficiency in microbiological tests for killing of airborne bacteria and fungal (*Aspergillus niger*) spores and found to kill >95% at a flow rate of about 150 m$^3$h$^{-1}$. The output of ozone has also been tested and been found to be within the EH38 guidelines.

EXAMPLE 2

Anti-Microbial Performance of an M4/4 Device

The invention has been developed into a range of devices designed for microbiological decontamination of atmospheres. This embodiment employs closed-coupled field technology for the contained generation of an oxidising field, in tandem with electrostatic filtration of the air stream. Combining these technologies in a manner that affords a high flow-rate permits the effective treatment of large volumes of atmosphere.

M4/4 Device

This embodiment of the invention comprises four fans connected and switched so as to be progressively activated in order to provide a range of airflow rates:

Speed 1=160 m$^3$/hour Speed 2=320 m$^3$/hour
Speed 3=480 m$^3$/hour Speed 4=540 m$^3$/hour Two modes of filtration were used in various experiments. Either a HEPA filter or an HAF (3M Filtrete™) post-filter were fitted and their relative effects compared.

Ozone Production Characteristics

The European standard for atmospheric levels of ozone is currently 0.2 ppm while, according to various literature sources the required dosage of ozone required to inactivate microbial systems, on contact, varies between 0.05 ppm and 0.4 ppm. An important aspect of this validation effort has been to demonstrate compliance of the device with European ozone emission standards, whilst additionally producing evidence of sufficient ozone generation to accommodate effective competence with regard to the task of broad scope anti-microbial activity.

A key advantage of the device is the claim that ozone generation and reactions with micro-organisms, occur contained solely within the device resulting in decontamination with no measurable emission of ozone.

Ozone Measurements

Ozone levels have been investigated employing a novel probe by which ozone production is determined by measurement of the degree of oxidation obtained with a d-☐ tocopherol coating during exposure. Trials have been conducted to measure ozone production within the device and the potential for environmental accumulation during use, with and without filter in situ.

TABLE 1

Measurement of ozone production by d-α tocopherol probe oxidation with filter in place

| Run Time hours | $O^3$ ppm within treatment chamber | $O^3$ ppm within 60 m³ Room |
|---|---|---|
| 0 | 24 | <0.2 |
| 6 | 103 | <0.2 |
| 12 | 94 | <0.2 |
| 18 | 107 | <0.2 |
| 24 | 102 | <0.2 |

TABLE 2

Measurement of ozone production by d-α tocopherol probe oxidation without filter in place

| Time hours | $O_3$ ppm within treatment chamber | $O_3$ ppm within 60 m³ Room |
|---|---|---|
| 0 | 41 | <0.2 |
| 6 | 96 | <0.2 |
| 12 | 97 | <0.2 |
| 18 | 104 | <0.2 |
| 24 | 106 | <0.2 |

Data indicate no significant emission of ozone from the device were detected over a 24 hour period in the operating environment. Measurements indicate that significantly higher levels of ozone are produced within the closed coupled field device than predictably are required for contact inactivation all classes of micro-organisms for which susceptibility has been published.

Microbiological Aspects of Filter Performance

Electrostatic air filtration is known to produce reduction in the levels air-borne microbial contaminants. A potential problem with stand-alone filtration devices is therefore the accumulation of possibly infective or otherwise unwanted viable contamination within the structure of the filter during life span. Trials conducted to monitor these possibilities generated the following data showing the recovery of differing classes of organism from the interior surfaces of the terminal filter during different periods of operation in waste processing room.

Conclusions

These data demonstrate that in an environment known to have high levels of air-borne microbial contamination no significant build up of viable organisms occurred in the filtration unit up to and including three months of use. This effect may caused by impingement of residual ozone on the active surfaces, loss of viability due to dehydration in the high flow rate of air, nutrient scarcity or a combination of these and other factors.

Such findings to some degree support the anti-microbial efficiency of the ozone generation system presented. More importantly these findings suggest that in respect of bacteria and fungi the filtration stage is unlikely to represent a biological hazard during replacement.

EXAMPLE 3

Single Pass Anti-Microbial Competence of M4/4 Device

The following experimental data reports on the performance of the device in relation to the reduction of single pass microbial challenges. Performance at each of four flow rates has been determined for a range of organisms with and without electrostatic filtration in place.

TABLE 4

M4/4 single pass performance with electrostatic filtration

| Organism | Challenge level cfu/l – 1 | Speed 1 Recovery cfu/l – 1 | Speed 2 Recovery cfu/l – 1 | Speed 3 Recovery cfu/l – 1 | Speed 4 Recovery cfu/l – 1 |
|---|---|---|---|---|---|
| A. niger | 8.80E+06 | <1 | <1 | <1 | <1 |
| S. typhimurium | 7.40E+06 | <1 | <1 | <1 | <1 |
| C. albicans | 6.00E+06 | <1 | <1 | <1 | <1 |
| S. aureus | 7.10E+06 | <1 | <1 | <1 | <1 |
| B. cereus | 2.20E+06 | <1 | <1 | <1 | 1.30E+02 |

TABLE 5

M4/4 Single performance with no electrostatic filtration

| Organism | Challenge level cfu/l – 1 | Speed 1 Recovery cfu/l – 1 | Speed 2 Recovery cfu/l – 1 | Speed 3 Recovery cfu/l – 1 | Speed 4 Recovery cfu/l – 1 |
|---|---|---|---|---|---|
| A. niger | 7.00E+06 | <1 | <1 | <1 | <1 |
| S. typhimurium | 8.40E+06 | <1 | <1 | <1 | <1 |
| C. albicans | 8.30E+06 | <1 | <1 | <1 | <1 |
| S. aureus | 9.20E+06 | <1 | <1 | <1 | <1 |
| B. cereus | 4.70E+06 | <1 | <1 | 3.10E+02 | 9.80E+02 |

Speed 1 = 160 m³/hour

TABLE 3

Recovery of viable micro-organisms from electrostatic filter material after differing periods of usage

| Operation interval | TVC cm³ Filter material | Moulds cm³ Filter material | Yeasts cm³ Filter material | Bacillus sp. cm³ Filter material | Gram neg sp. cm³ Filter material | Gram Pos sp. cm³ Filter material |
|---|---|---|---|---|---|---|
| 1 day | <10 | <10 | <10 | <10 | <10 | <10 |
| 1 week | <10 | <10 | <10 | <10 | <10 | <10 |
| 1 month | <10 | <10 | <10 | <10 | <10 | <10 |
| 4 months | <10 | 30 | <10 | 20 | <10 | 80 |

TABLE 5-continued

M4/4 Single performance with no electrostatic filtration

| Organism | Challenge level cfu/l – 1 | Speed 1 Recovery cfu/l – 1 | Speed 2 Recovery cfu/l – 1 | Speed 3 Recovery cfu/l – 1 | Speed 4 Recovery cfu/l – 1 |
|---|---|---|---|---|---|

Speed 2 = 320 m$^3$/hour
Speed 3 = 480 m$^3$/hour
Speed 4 = 540 m$^3$/hour

Conclusions

All conditions of treatment produced significant levels of reduction in the levels of air-borne challenges. Under these challenge conditions Speed 3 gave a 100% performance with filter in place while Speed 2 gave a 100% performance with no filter in place. With filter in place all organisms were reduced to non-detectable levels at increment 4 with the exception of *Bacillus cereus*, where only a 4 log reduction was achieved. It was noted that limiting the flow to Speed 3 (480 m$^3$/hour) with the filter in situ, guaranteed a consistent and rapid degree of air processing.

EXAMPLE 4

Single Pass Killing of Fungal Spores and Hyphae

Experimental Design

These experiments introduced a number of single calibrated doses of *Aspergillus niger* hyphal fragments and spore particles into a chamber having a 8 l$^{-1}$ volume. The chamber was constructed in a manner as to permit access of the Quest device intake grill to the interior of the chamber while the output section vented directly into a second chamber of identical volume. Both chambers were vented by membrane filters for the purpose of pressure equalisation. The purpose of the trial was to attempt to demonstrate a single pass efficiency in lethality in a known airborne pathogen.

Dosing Conditions

The biological material was delivered in the form of fungal hyphae and spores dispersed in calcium silicate matrix. Both chambers were equipped with fans intended to assist dispersion. Sampling was conducted via suction with collection in a 2% sucrose/saline solution an involved 2 L$^{-1}$ volume for each chamber. The device was not operational during dosing for 2 minutes after the introduction of the biological material but had been previously stabilised for 30 minutes. After the post-dose period the device was operated for period of 1 minute and after which the atmosphere in the delivery chamber was sampled.

Analysis

Recovery solutions were examined by serial dilution and survivors were estimated on oxytetracycline glucose yeast agar (5 days at 25° C.). The results of these counts provided estimates of the level of dosage and the level of survivors per 1$^{-1}$ of atmosphere before and after treatment.

Results

Tables 6 and 7 present the data obtained in this trial for instances of the device operating with either the electrostatic or HEPA filter in place.

TABLE 6

Single pass efficiency for *Aspergillus niger* (mixed hyphae and spores) employing Electrostatic filtration and $O_3$ dosing

| Challenge level cfu/l$^{-1}$/air pre in take | Recovery level cfu/l$^{-1}$/air post filter | Percentage Kill |
|---|---|---|
| 8.3E+05 | 7.6E+04 | 90.807 |
| 4.2E+05 | 2.0E+03 | 99.524 |
| 6.1E+05 | 4.1E+03 | 99.328 |
| 7.3E+05 | 9.2E+03 | 98.740 |
| 7.2E+05 | 6.2E+03 | 99.139 |
| 7.4E+05 | 7.1E+03 | 99.041 |
| 8.2E+05 | 8.4E+03 | 98.976 |
| 6.3E+05 | 9.2E+03 | 98.540 |
|  | Mean | 98.012 |

TABLE 7

Single pass efficiency for *Aspergillus niger* (mixed hyphae and spores) employing HEPA filtration and $O_3$ dosing

| Challenge level cfu/l$^{-1}$/air pre in take | Recovery level cfu/l$^{-1}$/air post filter | Percentage Kill |
|---|---|---|
| 5.5E+05 | 8.0E+01 | 99.985 |
| 6.1E+05 | 9.0E+01 | 99.985 |
| 2.8E+05 | 3.0E+01 | 99.989 |
| 6.1E+05 | 9.0E+01 | 99.985 |
| 6.3E+05 | 8.0E+01 | 99.987 |
| 5.2E+05 | 8.0E+01 | 99.985 |
| 6.3E+05 | 1.1E+02 | 99.983 |
| 5.8E+05 | 5.0E+01 | 99.991 |
|  | Mean | 99.986 |

EXAMPLE 5

Continuous Dosage Lethality with a Range of Micro-Organisms

In this series of trials a wide range of microbial types was continuously introduced at the intake section of the M4/4 device for a period of 1 hour. During the exposure time periodic measurements were taken at the output section and the levels of survivors determined. The following results were obtained.

TABLE 8

M4/4 performance: continuous input of bacteria and fungi

| Organism | Class | Mean cfu/m$^3$/Hr at input Treatment stream | Mean cfu/m$^3$/Hr post Treatment exit stream | Mean decline Log/cfu/m$^3$/Hr post Treatment exit stream | Apparent percentage reduction |
|---|---|---|---|---|---|
| *Escherichia coli* | Gram – ve | 2.1E+05 | 0.0E+00 | >5 | >99.999 |
| *S. tyhpimurium* | Gram – ve | 4.6E+05 | 0.0E+00 | >5 | >99.999 |
| *E. agglormerans* | Gram – ve | 3.9E+05 | 0.0E+00 | >5 | >99.999 |
| *E. gergoviae* | Gram – ve | 4.2E+05 | 0.0E+00 | >5 | >99.999 |
| *A. aerogens* | Gram – ve | 7.1E+05 | 0.0E+00 | >5 | >99.999 |

TABLE 8-continued

M4/4 performance: continuous input of bacteria and fungi

| Organism | Class | Mean cfu/m$^3$/Hr at input Treatment stream | Mean cfu/m$^3$/Hr post Treatment exit stream | Mean decline Log/cfu/m$^3$/Hr post Treatment exit stream | Apparent percentage reduction |
|---|---|---|---|---|---|
| S. marcescens | Gram − ve | 8.2E+05 | 0.0E+00 | >5 | >99.999 |
| E. sakazakii | Gram − ve | 3.4E+05 | 0.0E+00 | >5 | >99.999 |
| E coli 0157 H:7 | Gram − ve | 3.5E+05 | 0.0E+00 | >5 | >99.999 |
| P. aeruginosa | Gram − ve | 6.1E+05 | 0.0E+00 | >5 | >99.999 |
| P. putida | Gram − ve | 8.2E+05 | 0.0E+00 | >5 | >99.999 |
| S. aureus oxford | Gram + ve | 4.3E+05 | 0.0E+00 | >5 | >99.999 |
| S. aureus MSRA | Gram + ve | 4.8E+05 | 0.0E+00 | >5 | >99.999 |
| S. epidermidis | Gram + ve | 3.7E+05 | 0.0E+00 | >5 | >99.999 |
| M. luteus | Gram + ve | 9.0E+05 | 0.0E+00 | >5 | >99.999 |
| S. faecalis | Gram + ve | 7.3E+05 | 0.0E+00 | >5 | >99.999 |
| S. pyogenes | Gram + ve | 3.6E+05 | 0.0E+00 | >5 | >99.999 |
| B. cereus | Gram + ve | 7.1E+05 | 0.0E+00 | >5 | >99.999 |
| B. globigii | G + ve Spore | 7.9E+05 | 1.0E+01 | >5 | 99.999 |
| B. subtilis | G + ve Spore | 2.1E+05 | 3.0E+01 | >5 | 99.986 |
| B. megaterium | G + ve Spore | 6.2E+05 | 9.0E+01 | >5 | 99.985 |
| S. cerevisiea | Yeast | 4.3E+05 | 0.0E+00 | >5 | >99.999 |
| S. bailli | Yeast | 7.2E+05 | 0.0E+00 | >5 | >99.999 |
| Pichia mixed sps | Yeast | 6.3E+05 | 0.0E+00 | >5 | >99.999 |
| S. ludwigii | Yeast | 6.0E+05 | 0.0E+00 | >5 | >99.999 |
| A. niger | Mould mycelial | 6.2E+05 | 0.0E+00 | >5 | >99.999 |
| A. flavus | Mould mycelial | 7.8E+05 | 0.0E+00 | >5 | >99.999 |
| F. poea | Mould mycelial | 7.2E+05 | 0.0E+00 | >5 | >99.999 |
| P. digitatum | Mould mycelial | 6.9E+05 | 0.0E+00 | >5 | >99.999 |
| F graminerium | Mould mycelial | 4.3E+05 | 0.0E+00 | >5 | >99.999 |
| A. niger | Mould Spore | 8.2E+05 | 7.0E+01 | >5 | 99.991 |
| A. flavus | Mould Spore | 6.7E+05 | 5.0E+01 | >5 | 99.993 |
| F. poea | Mould Spore | 8.2E+05 | 0.0E+00 | >5 | >99.999 |
| P. digitatum | Mould Spore | 6.7E+05 | 0.0E+00 | >5 | >99.999 |
| F graminerium | Mould Spore | 2.9E+05 | 0.0E+00 | >5 | >99.999 |

TABLE 9

M4/4 performance: continuous input of viral particles

| Organism | Class | Mean cfu/m$^3$/Hr at input Treatment stream | Mean cfu/m$^3$/Hr post Treatment exit stream | Mean decline Log/cfu/m$^3$/Hr post Treatment exit stream | Apparent Percentage reduction |
|---|---|---|---|---|---|
| CTX | SS DNA | 4.3E+12 | 8.1E+02 | >12 | >99.999 |
| ScV-L-BC | DS RNA | 9.2E+12 | 4.6E+02 | >12 | >99.999 |
| FcoV (attenuated) | SS + RNA | 7.1E+12 | 3.0E+02 | >12 | >99.999 |
| T4 Phage | DS DNA | 5.3E+12 | 7.4E+02 | >12 | >99.999 |

Conclusions

The device demonstrated a high level of competence in the inactivation of a wide range of micro-organisms including bacterial cells, bacterial spores, viral particles, mould, mould spores and yeasts. Kill efficiencies in excess of Log 12 were obtained consistently for all classes of viral particle examined, while for all other classes of organism no less than a Log 5 kill was obtained on a continuous basis. In summary, the device is highly effective at killing micro-organisms.

EXAMPLE 6

Sanitisation of a Laboratory Incubator Room

Introduction

In spite of good compliance with GLP standards laboratories may still develop problems associated with airborne microbial contamination. Usually such problems are detected by routine environmental surveillance or incidences of contamination on solid agar plates.

In this study a problem was investigated relating to a persistent environmental contamination in a commercial grain testing laboratory. This facility had reported significant levels of mould contamination of both blank plates and plates intended for the isolation of yeasts and moulds from samples. In-house environmental analysis by settle plate determined the presence of identical isolates to those found on the plates in the atmosphere of the incubation room. The isolate responsible for the contamination was confirmed as *Fusarium poae*. This organism is common in temperate regions and is associated with commodities such as wheat and maize, both of which were commonly handled by the facility. It demonstrates growth over the range 2.5°-33° C. and, characteristically, produces profuse growth with salmon or pale pink colonies on common mycological media.

Trial Outline

The trial was conducted in two stages. During the first month of monitoring the M4 device was not in operation and air sampling was conducted on an hourly basis between the hours of 9.00 am and 6.00 pm over a six-day working week. Sampling was conducted employing a Cassela volumetric sampler with impaction onto oxytetracycline glucose yeast agar. During week one (device off) 0.1, 0.2, and 0.5 L-1 air volumes were taken at the specified intervals.

The device was operative during month two. Sampling was conducted to the same schedule described above with an identical sampling procedure. Simultaneously, during the trial records were kept of non-compliant contaminated agar intended for use in analytical procedures.

| | | Results | |
|---|---|---|---|
| Device status | Week | F. poae cfu/L$^{-1}$/air | Percentage in lab plate contamination |
| OFF | 1 | 17100 | 3 |
| OFF | 2 | 21300 | 2 |
| OFF | 3 | 16700 | 9 |
| OFF | 4 | 18900 | 3 |
| | Mean | 18500 | 4.25 |
| ON | 5 | 20 | <1 |
| ON | 6 | 40 | <1 |
| ON | 7 | 2 | <1 |
| ON | 8 | 3 | <1 |
| | Mean | 16.25 | <1 |

Conclusions

In this laboratory an overt problem had been experienced in relation to media contamination which was directly related to environmental cross-contamination with *Fusarium poae*. The operation of the M4/4 device in the area that was the source of this problem successfully reduced the level of contamination on a consistent basis by between 2 and 3 log cycles L-1 air. This magnitude of effect was sufficient to reduce the level of media contamination to a non-detectable level. On this basis, the M4/4 device has been shown to be an effective tool in the maintenance of a microbiological laboratory air quality.

EXAMPLE 7

Sanitisation of the Atmosphere in a Class Microbiological Laboratory Waste Room

Introduction

A device according to the invention with a free fan transfer volume of 190 m3/hour fitted with either replaceable electrostatic (flow rate=160 m3/hour) or HEPA (flow rate=65 m3/hour) post-filters was subjected to a practical evaluation in a Class II microbiological laboratory waste room.

It was theorised that usage of electrostatic filtration in combination with a closed coupled field oxidation field would afford both reduction of airborne micro-organisms as well as good odour decontamination characteristics while employment of HEPA filtration was anticipated to produce superior microbiological performance. Assessment was by monitoring the reduction of airborne Gram-negative bacteria over a seven day period in a microbiological laboratory waste-processing room. Measurement included the performance characteristics of both filtration systems.

The vast majority of contemporary microbiological laboratories are equipped with a designated area designed to afford physical segregation of contaminated biological waste intended for sanitation by autoclaving preceding safe disposal. Such waste consists of agar plates, cultures and implements employed in microbiological manipulations. In general, such waste is extremely biologically active prior to treatment and may contain billions of organisms per gram. While every effort in GLP is to prevent transfer of contaminants, the nature of the autoclaving process requires that storage bags are open to the atmosphere at the start of processing. As a consequence, the opportunity exists for the introduction of large masses of organisms or spores into the environment. Factually, such areas exhibit high levels of airborne contamination.

These distribution factors coupled with the thermal currents created by autoclave operation engender a demonstrably abundant and sustained level of airborne micro-organisms of many differing types. It is true that such contamination is unlikely to present as a direct health risk through inhalation but such an environment provides a useful model for efficiency studies of devices, which purport to reduce airborne levels of micro-organisms.

In this trial, the regime involved the sampling of the atmosphere in the test environment by impaction of air onto the surface of agar plates through the use of a Cassela air-sampling device. The Cassela unit is capable of accurately sampling a known volume of atmosphere over a 30 second period and continuously delivering the sampled air to an enclosed chamber. In this chamber an agar plate is exposed to column of intake air whilst rotating, thus distributing micro-organisms evenly over the surface of the plate. Subsequent incubation of the plates allows enumeration of organisms present in the original volume of atmosphere examined. Through the use of differing types of agar and diagnostic tests, it is possible to differentially count different types or classes of micro-organism.

Room Conditions

The room comprised a 24.3 m3 cube. It contained an autoclave with treated waste in one half and 25 kg storage bags of untreated waste in the remaining floor area. At any one time the area contained a minimum of 16 untreated waste bags, of which between 8 and 10 bags were be handled and processed in a working day between the hours of 9.00 am and 6.00 pm. The sampling device was located centrally. Normally the room atmosphere was vented by forced extraction, but this was suspended during the trial. The autoclave hot exhaust was vented via an enclosed circuit, which was not thought to affect the atmospheric composition of the test environment.

Sampling Plan

Sampling occurred over a twenty-four hour period at the intervals given in Table 11 below. Such sampling extended over a seven-day period with the device running without any form of filtration in place and without the ozone generator switched on, to demonstrate the background level of contamination. The data obtained are given in Tables 11 and 13 below. The data gathered in this exercise were employed as the comparison set for all information gathered during the subsequent period when the device was operational as a sanitising unit.

Two further identically-scheduled sampling periods were conducted sequentially separated by a four day recovery gap. Firstly, the device was operated with the corona discharge unit on and an electrostatic filter in place. In the second session the device was operated with a HEPA filter in place, again with an identical sampling plan.

Microbiological Analysis

The agar employed in all tests was Violet Red bile glucose agar (VRBGA) intended for the recovery of Gram-positive organisms from the atmosphere through the use of the Cassela device. Colonies were recovered on this agar after incubation at 35° C. for 24 hours. As the trials were intended primarily to show overall comparisons, it was assumed that all isolates obtained on VRBGA were Gram-negative and all isolates were counted. Colonies were further differentiated on the basis of oxidase reaction. All sampling was conducted in duplicate.

Results

Table 11 below presents the data obtained for Gram-negative (Ox +ve and Ox −ve) isolates during the unsanitised control period and that for the data obtained during the period of oxidation treatment associated with electrostatic filtration of the return air flow. Table 12 illustrates the average percentage kill through out the day attributable to the action of oxidation treatment and electrostatic filtration. Tables 13 and 14 summarise the same categories of data obtained for the period when sanitisation was attempted employing oxidation and HEPA filtration.

TABLE 11

Mean microbial levels over a 24 hour period in a microbiological waste room (23.4 m3) with and without continuous operation of device with electrostatic filtration

| Time | Condition | Oxidase Pos Gram negative isolates $L^{-1}$ air | Oxidase Neg Gram negative isolates $L^{-1}$ air |
| --- | --- | --- | --- |
| 06:00 AM | $o_3$ off EF− | 4.7E+03 | 8.6E+03 |
| 10:00 AM | $o_3$ off EF− | 5.6E+03 | 9.2E+03 |
| 02:00 PM | $o_3$ off EF− | 9.8E+03 | 2.8E+04 |
| 06:00 PM | $o_3$ off EF− | 2.0E+04 | 3.7E+04 |
| 08:00 PM | $o_3$ off EF− | 1.8E+04 | 3.3E+04 |
| 02:00 AM | $o_3$ off EF− | 9.2E+03 | 1.9E+04 |
| 04:00 AM | $o_3$ off EF− | 3.7E+03 | 8.7E+03 |
| 06:00 AM | $o_3$ on EF+ | 6.0E+02 | 1.3E+03 |
| 10:00 AM | $o_3$ on EF+ | 7.7E+02 | 1.3E+03 |
| 02:00 PM | $o_3$ on EF+ | 1.6E+03 | 4.4E+03 |
| 06:00 PM | $o_3$ on EF+ | 3.4E+03 | 6.2E+03 |
| 08:00 PM | $o_3$ on EF+ | 3.4E+03 | 5.8E+03 |
| 02:00 AM | $o_3$ on EF+ | 1.4E+03 | 3.0E+03 |
| 04:00 AM | $o_3$ on EF+ | 4.8E+02 | 1.2E+03 |

TABLE 12 mean microbial % reduction levels over a 24 hour period in a microbiological waste room (23.4 m3) with device operating with electrostatic filtration

| Time | Condition | Oxidase Pos Gram negative isolates $L^{-1}$/air | Oxidase Neg Gram negative isolates $L^{-1}$/air |
| --- | --- | --- | --- |
| 06:00 | $o_3$ on EF+ | 87.3 | 85.1 |
| 10:00 | $o_3$ on EF+ | 86.2 | 85.4 |
| 14:00 | $o_3$ on EF+ | 83.2 | 84.3 |
| 18:00 | $o_3$ on EF+ | 82.8 | 83.2 |
| 20:00 | $o_3$ on EF+ | 81.3 | 82.2 |
| 02:00 | $o_3$ on EF+ | 85.3 | 84.6 |
| 04:00 | $o_3$ on EF+ | 86.9 | 85.8 |

TABLE 13 mean microbial levels over a 24 hour period in a microbiological waste room (23.4 m3) with and without continuous operation of device with HEPA filtration

| Time | Condition | Oxidase Pos Gram negative isolates $L^{-1}$/air | Oxidase Neg Gram negative isolates $L^{-1}$/air |
| --- | --- | --- | --- |
| 06:00 | $o_3$ off HEPA− | 4.7E+03 | 8.6E+03 |
| 10:00 | $o_3$ off HEPA− | 5.6E+03 | 9.2E+03 |
| 14:00 | $o_3$ off HEPA− | 9.8E+03 | 2.8E+04 |
| 18:00 | $o_3$ off HEPA− | 2.0E+04 | 3.7E+04 |
| 20:00 | $o_3$ off HEPA− | 1.8E+04 | 3.3E+04 |
| 02:00 | $o_3$ off HEPA− | 9.2E+03 | 1.9E+04 |
| 04:00 | $o_3$ off HEPA− | 2.1E+03 | 8.7E+03 |
| 06:00 | $o_3$ On HEPA+ | 3.1E+03 | 5.7E+03 |
| 10:00 | $o_3$ On HEPA+ | 3.9E+03 | 6.2E+03 |
| 14:00 | $o_3$ On HEPA+ | 7.0E+03 | 2.0E+04 |
| 18:00 | $o_3$ On HEPA+ | 1.6E+04 | 2.8E+04 |
| 20:00 | $o_3$ On HEPA+ | 1.5E+04 | 2.7E+04 |
| 02:00 | $o_3$ On HEPA+ | 6.5E+03 | 1.4E+04 |
| 04:00 | $o_3$ On HEPA+ | 1.4E+03 | 5.7E+03 |

TABLE 14 mean microbial % reduction levels over a 24-hour period in a microbiological waste room (23.4 m3) with device operating with HEPA filtration.

| | | | |
| --- | --- | --- | --- |
| 06:00 | $o_3$ On HEPA+ | 34.5 | 33.9 |
| 10:00 | $o_3$ On HEPA+ | 30.3 | 33.1 |
| 14:00 | $o_3$ On HEPA+ | 28.6 | 28.7 |
| 18:00 | $o_3$ On HEPA+ | 22.1 | 24.6 |
| 20:00 | $o_3$ On HEPA+ | 19.2 | 17.4 |
| 02:00 | $o_3$ On HEPA+ | 29.6 | 28.2 |
| 04:00 | $o_3$ On HEPA+ | 34.8 | 34.2 |

Conclusions

The data given in tables 11-14 indicate that the test environment under conditions of no treatment did exhibit elevated levels of airborne microbial contamination. In the same tables it is observed that irrespective of the filter type employed with device, measurable reduction of airborne levels of Gram negative bacteria was achieved. On a continuous use basis with active replacement of micro-organisms into the environment, operation with electrostatic filtration gave an average of 84% reduction of gram negative bacteria (Ox +ve and −ve). This amounts to a continuos overall reduction of between 1 and 2 log cycles. By comparison the unit gave only 28% reduction when operated with HEPA. filtration.

In theory, HEPA filtration should provide greater efficiency with respect to microbial removal but under the trial conditions we calculated that with this form of filtration in place the device was capable of only 2.7 room changes per hour. It is apparent this was an insufficient flow rate to achieve high levels of reduction in an environment to which micro-organisms are constantly being added.

In the case of operation with electrostatic filtration 7.1 room changes per hour were obtained, a factor which produced a much higher degree of impingement on the levels of airborne gram negative bacteria:

Both forms of filtration gave very high kill efficiencies during the single pass trials with *Aspergillus niger*. In this case HEPA in combination with ozonation gave 99.986% reduction of challenge, which is close to the theoretical performance. On the other hand electrostatic filtration in combination with ozonation gave 98.012% reduction of challenge.

Overall, the data favour the combination of closed coupled filed oxidation with electrostatic filtration. This configuration affords high flow rates with very high levels of kill in an environment where recontamination of sanitised air is continuous. By comparison with other commercial units the kill rate in the waste room environment may be considered very significant.

EXAMPLE 8

Odour-Removing Apparatus

The principle of drawing air through a field of high oxidation potential sufficient to oxidise many organic pollutants is equally applicable to the removal of unpleasant or unwanted odours, where these are caused by compounds capable of being oxidised to odourless products. The apparatus of the invention, optionally fitted with pre- and/or post-filters, preferably containing activated charcoal is highly suitable for this purpose.

Trial Outline

A sensory evaluation was conducted each day during operation of an M4/4 device in the microbiological waste processing facility. This involved subjective scoring by four people according to the Key given with Table 15, below. Evaluations were made for each type of filter and with the closed coupled oxidising field operating.

TABLE 15

Sensory appreciation scores obtained during operation of device with either electrostatic filtration or HEPA

| Day | Electrostatic | HEPA |
| --- | --- | --- |
| 0 | 1 | 1 |
| 1 | 3 | 2 |
| 2 | 6 | 2 |
| 3 | 6 | 3 |
| 4 | 6 | 2 |
| 5 | 6 | 3 |
| 6 | 6 | 2 |
| 7 | 6 | 3 |

Key to scores
1 Unpleasant
2 Change perceived but unpleasant
3 Improvement
4 Acceptable but some odour detected
5 Acceptable environment
6 Markedly improved odour free

EXAMPLE 9

Apparatus for the Removal of Smoke Particles from Air

Introduction

The apparatus based in the casing shown in FIG. 3 may be configured for the efficient removal of smoke from air. In this embodiment the fans may be so arranged as to draw air in through the circular apertures, preferably through a pre-filter, through the field of high ozone concentration and either out through the louvred apertures shown or back out through a post-filter arrangement.

In one embodiment, particularly suitable for use in public areas such as public houses, hotels and bars is illustrated in FIG. 4. This apparatus (the 'P6' model) is configured with two fans drawing air in through the filter assembly (i.e. there is a pre-filter) expelling air out through a different area of the filter assembly (ie the air is also post-filtered). The capacity of the apparatus is approximately 380 m3 per hour. The filter assembly comprises an outer low pressure 3M 3202 WAT tobacco smoke filter and an inner 3M Filtrete™ HAF electrostatic filter.

Another, particularly preferred, embodiment is the 'P8' device, which has four fans and is configured to draw air in through a filter assembly, preferably as described above, air being expelled through louvred apertures. The capacity of the apparatus is approximately 760 m3 per hour.

The core components of fan, closed coupled field unit and filters are common with the apparatus of Example 1.

Study Design

The efficiency of the device in reduction of eight types of tobacco-related toxic substances was tested in a test environment. These substances primarily occur in the atmosphere due to combustion of tobacco and the associated exhalation of smoke from combusted tobacco. A list of the analytes determined is given in Table 17 below.

The test environment consisted of a public house pool room with a volume of 84 m3 into which the P8 unit was installed. During the operation the device, per specification, was predicted to change and process the environment within this room at a rate 9 times per hour. Common practice prior to the trial was to evacuate the atmosphere by forced and passive ventilation. These systems of air purification were considered unsatisfactory by the proprietor of the property, especially during the winter, due to the requirement to compensate for massive heat loss.

After installation of the P8 device, air sampling was conducted in the pool room for seven days, between the hours of 8.00 pm and 9.00 pm at a rate of 5 m3 per hour, without the device in operation. This provided background control data for all analytes. A further set of control data was obtained at 5.0 pm which represents a point after normal ventilation when the room is not used for pool or smoking. The data relating to this point may be considered base level for all analytes. During the subsequent seven days the sampling procedure was repeated with the device in operation, with the goal of determining the efficiency of atmospheric clean up. During the trial an estimate was made of the daily cigarette consumption during the sampling interval. Sampling was conducted by the use of a vacuum device with collection of sampled atmosphere in either phosphate buffer or an acetonitrile:methanol phase. Analytes were determined quantitatively employing the following analytical techniques: gas/liquid chromatography, HPLC diode array and differential pulse polarography.

Results

Table 16 below describes the pattern of cigarette consumption recorded for the test environment during the sampling periods. Table 17 describes the mean levels of analytes recorded during the control period and during the period of sampling when the P8 device was activated. This table also describes the contribution to air quality attributable to the device in terms of percentage reduction of airborne toxic substances.

TABLE 16

Mean cigarette consumption in a public house pool room between 8.00 PM and 9.00 PM

| Day | Cigarette consumption per hour |
| --- | --- |
| Monday | 5 |
| Tuesday | 11 |
| Wednesday | 7 |
| Thursday | 9 |

TABLE 16-continued

Mean cigarette consumption in a public house
pool room between 8.00 PM and 9.00 PM

| Day | Cigarette consumption per hour |
|---|---|
| Friday | 19 |
| Saturday | 23 |
| Sunday | 16 |
| Mean | 13 |

TABLE 17

Mean level of tobacco smoke analytes in the atmosphere in a public house pool
room for a seven day period with and without the P8 unit in operation

| ANALYTE | UNIT | Mean level 5PM No treatment Device off | Mean level 9PM No treatment Device off | Mean level 9PM with treatment Device on | Mean reduction due to treatment |
|---|---|---|---|---|---|
| Carbon monoxide | Mg/m$^3$ | 0.82 | 7.1 | 0.4 | 94.4 |
| 3-ethenylpyridine | Mg/m$^3$ | 0.17 | 37.6 | 0.4 | 98.9 |
| Formaldehyde | Mg/m$^3$ | 0.33 | 84.2 | 0.2 | 99.8 |
| Acetaldehyde | Mg/m$^3$ | 0.01 | 196.3 | 0.4 | 99.8 |
| Ammonia | Mg/m$^3$ | 0.01 | 103.5 | 0.8 | 99.2 |
| Nicotine | Mg/m$^3$ | 0.96 | 61.4 | 1.06 | 98.3 |
| Total phenolics | Mg/m$^3$ | 0.11 | 12.7 | 0.2 | 98.4 |
| Total cresols | Mg/m$^3$ | 0.06 | 3.8 | 0.08 | 98.9 |

Discussion

The test data demonstrates that operation of the P8 device produced highly significant reduction in all levels of tobacco smoke analytes with overall analyte clearance rates over the range 97.9 to 99.8%. The level of reduction is such that the residue levels during device operation are not significantly different from background level during periods when the room was in disuse. Considering the findings and that there was virtually constant replacement of the analytes to the atmosphere, P8 device performed in a highly efficient manner in the removal of toxic tobacco smoke contaminants.

EXAMPLE 10

Duct-Mounted Apparatus

A particularly useful application of the invention is its incorporation into air-conditioning ducting in buildings and, in particular, in aircraft. A preferred embodiment comprises a cartridge assembly, through which air flows, comprising one or more corona discharge unit as herein described, optionally with one or more filter assemblies. In this situation, the pressure within the duct may be sufficient to allow a suitable flow of air through the cartridge assembly without the further use of fans or impellors. It has been found that one 5 W corona discharge unit, as described, per approximately 500 m3 per hour throughput of air is suitable. Such units are useful in clearing air of micro-organisms, odours, and smoke.

EXAMPLE 11

Levels of Ozone Leakage: Active and Passive Sampling

A: Active Sampling
Tests Performed

The leakage of ozone from an operating AM4 unit (190 m$^3$ h$^{-1}$ airflow, one 5 W corona discharge unit) was measured when the air filtration system was operated in 4 different modes: (i) filter in and corona discharge unit on; (ii) filter out and corona discharge unit on; (iii) filters in and corona discharge unit off, and (iv) filters out and corona discharge unit off.

The ozone levels were measured at 0, 0.5 and 1.0 m from the emitting face of the unit. The distance was measured using a meter rule and was checked at intervals during the experiment by the operator. The experiment was performed on 19 Jun. 2002 in a laboratory that was at a temperature of 22° C. The ozone measurement was performed using Gastec detection tubes (No. 18L). The 18L range provides a rapid, fully quantitative analysis of the concentration of ozone in air with an accuracy of ±25%. The manufacturer states that the minimum detectable concentration as 0.01 ppm. The Gastec tubes were purchased specifically for this work and were marked valid until May 2005. A Gastec multi-stroke gas sampling pump was used in conjunction with the tubes.

The principle of the gas tube operation is described by equation 1 below.

$$2O_3 + C_{16}H_{10}N_2O_2 \rightarrow 2C_8H_5NO_2 + 2O_2 \qquad \text{Eqn (1)}.$$

The ozone in air, once sucked up through the tube, bleaches the indigo ($C_{16}H_{10}N_2O_2$, blue) to form isatin ($C_8H_5NO_2$), which is white in colour.

For each position, i.e. 0, 0.5 and 1.0 m from the emitting surface, (at an approximate angle of 90°) and each operational mode, a tube was placed in the pump and held in position manually. The system was left to stabilize for 5 minutes and then 10 pumps (equivalent to 1000 cm$^3$ volume) were drawn on the hand pump. Each pump lasted an average of 30 seconds. The measurement for each combination of position and operational mode was repeated five times.

Results

The individual results for each tube are shown in Table 18.

TABLE 18

Individual raw results (ppm) for the Gastec tubes.

| Running mode | Order[1] | Replicate results (ppm) | | | | | Mean (ppm) | Actual value[2] (ppm) |
|---|---|---|---|---|---|---|---|---|
| | | 1 | 2 | 3 | 4 | 5 | | |
| Filter in; corona on | | | | | | | | |
| 0 m | 4$^{th}$ | 0.1 | 0.1 | 0.1 | 0.1 | 0.1 | 0.1 | 0.05 |
| 0.5 m | 5$^{th}$ | 0 | 0 | 0 | 0 | 0 | 0 | 0 |

TABLE 18-continued

Individual raw results (ppm) for the Gastec tubes.

| Running mode | Or-der[1] | Replicate results (ppm) | | | | | Mean (ppm) | Actual value[2] (ppm) |
|---|---|---|---|---|---|---|---|---|
| | | 1 | 2 | 3 | 4 | 5 | | |
| 1.0 m Filter out; corona on | 6th | 0 | 0 | 0 | 0 | 0 | 0 | 0 |
| 0 m | 3rd | <0.05 | <0.05 | <0.05 | <0.05 | <0.05 | <0.05 | <0.025 |
| 0.5 m | 7th | 0 | 0 | 0 | 0 | 0 | 0 | 0 |
| 1.0 m Filter in; corona off | 8th | 0 | 0 | 0 | 0 | 0 | 0 | 0 |
| 0 m | 1st | 0 | 0 | 0 | 0 | 0 | 0 | 0 |
| 0.5 m | 11th | 0 | 0 | 0 | 0 | 0 | 0 | 0 |
| 1.0 m Filter out; corona off | 12th | 0 | 0 | 0 | 0 | 0 | 0 | 0 |
| 0 m | 2nd | 0 | 0 | 0 | 0 | 0 | 0 | 0 |
| 0.5 m | 9th | 0 | 0 | 0 | 0 | 0 | 0 | 0 |
| 1.0 m | 10th | 0 | 0 | 0 | 0 | 0 | 0 | 0 |

[1]this shows the order in which the replicates where run.
[2]As 10 pumps were used, the values read from the tubes were halved as per the manufacturers instructions.

Discussion and Conclusions

The readings were very small such that the highest readings only coloured the first graduation on the Gastec tube. The highest reading was recorded when the tube was placed at the emitting surface and the filter was in and the korona was on. The next highest reading was recorded with the korona on, but the filter out. All other positions and operational combinations produced no change of colour on the Gastec tube indicating the levels of ozone, if present, were less than 0.01 ppm. The average gap in the Gastec tube through which the air is drawn was 1 mm. The analysis system used is known as active sampling. Five replicate tubes were used for each combination to help account for the potential variability in the positioning of the Gastec tube within the flow of air exiting from the air filtration system.

B: Passive Sampling

Tests Performed

The tests are were designed to determine whether a significant concentration of ozone accumulated in a confined space in which an AM4 unit operated over an 8 hour period as measured by passive sampling.

The test was performed in a room of approximately 36.75 $m^3$ (3.5 m×3.5 m×3.0 m) receiving minimal natural light. Ozone was measure by a number of sampling cards (AFC International Inc, USA).

1. ChromAir ozone cards
2. ChromAir nitrogen cards
3. SafeAir ozone cards
4. SafeAir nitrogen dioxide cards Nitrogen dioxide is a potential positive interferent beyond 0.3 ppm with both ozone sampling cards and so its concentration was also monitored. Average room temperature 19° C. Sample cards were placed randomly on the floor, walls and suspended from the ceiling of the room; The cards were monitored for 8 hours with and without the unit operating. Monitoring was every 15 minutes for the first hour and then after a further 7 hours.

Results

Unit Off:

ChromAir ozone cards: 0.08* ppm (0.01 ppm/h)
SafeAir ozone cards: no change detected
Nitrogen Dioxide: none detected
*Lowest recordable concentration=background Unit On:

ChromAir ozone cards: 0.40 ppm (0.05 ppm/h)
SafeAir ozone cards: qualitative change indicating ozone detected
Nitrogen Dioxide: none detected Overall Ozone Levels:

'Unit on'–'Unit off' values=0.04 ppm time weighted average over 8 hour period

Discussion

HSE occupational exposure limit (OEL) for ozone over an 8 hour period is 0.2 ppm and the 15 minute exposure limit is set at 0.4 ppm. The recorded ozone leakage in the experiment was therefore well within (20%) the 8 hour exposure limit.

The invention claimed is:

1. An apparatus for the treatment of air comprising a low power alternating current corona discharge ozone generator that has a power rating in the range of 4 watts to 50 watts mounted inside a chamber, the chamber being defined by an earthed casing comprising a metal or a plastics material impregnated or coated with a metallic material and having an air inlet and an air outlet, wherein the inlet and outlet are disposed in proximity to each other and the apparatus provided with a single filter mounted so that respective different portions of the filter occlude the inlet and outlet, respectively, and at least one air flow impeller formed and arranged for inducing a flow of air through said chamber from inlet to outlet in a non-rectilinear path, said ozone generator being formed and arranged for generating a restricted concentration of ozone and any other reactive species formed together therewith, within an inactivating zone contained within said chamber, through which said air flow is passed in use of said apparatus, which restricted concentration is sufficient effectively to inactivate airborne pollutant material entrained in said air flow, yet which restricted concentration decays sufficiently outside said inactivating zone so that the concentration of ozone in the cleaned air expelled from said apparatus is less than about 0.3 ppm without the use of an ozone decomposition catalyzer.

2. The apparatus of claim 1 wherein said low power corona discharge ozone generator comprises a low power corona discharge device provided with a low power high voltage output transformer.

3. The apparatus of claim 2 wherein the low power corona discharge device comprises concentric tubular metal gauze electrodes separated by a tubular strengthened glass dielectric.

4. The apparatus of claim 3 wherein the glass dielectric is of titanium dioxide strengthened borosilicate glass.

5. An apparatus according to claim 1 wherein said air flow impeller is formed and arranged so as to provide a flow rate of air through the apparatus in the range 50-2500 $m^3$ per hour.

6. An apparatus according to claim 1 wherein said at least one filter is adapted for removing tobacco smoke oil and/or tar.

7. An apparatus according to claim 1 wherein said filter is an electrostatic filter.

8. An apparatus according to claim 1 wherein is used for said alternating current corona discharge ozone generator, an AC supply with a frequency in the range from 50 to 1000 Hz.

9. An apparatus according to claim 1 wherein is used an AC supply with an operating voltage in the range from 1 to 6 kV.

10. An apparatus according to claim 1 wherein is used an AC supply providing a (starting) current in the range from 1 to 10 mA.

11. An apparatus according to claim 1 wherein is used an air flow impeller formed and arranged for inducing a flow of air through said chamber, in use of the apparatus, which air flow has a residence time in said chamber in the range from 0.2 to 20 seconds.

12. An apparatus according to claim 1 wherein is used a low power corona discharge device with a solid dielectric.

13. A method of cleaning air comprising the steps of:
providing an apparatus according to claim 1;
powering the ozone generator of said apparatus so as to generate ozone in the inactivation zone of said apparatus;
operating said airflow impeller so as to pass a flow of said air through said inactivation zone; and
exhausting the air from the inactivation zone through a catalyst-free decomposing zone in said chamber.

14. An ozone-based device for treating pollutants in air comprising:
a grounded, conductive, enclosed chamber having an air inlet and an air outlet arranged to produce air flow therebetween; said inlet and outlet being arranged in close proximity to receive a single filter with respective portions occluding the inlet and outlet.
an impeller having a motor for producing said flow;
an inactivating zone within said chamber proximate said inlet;
a low power ozone generator within the inactivating zone and in said flow, wherein said generator operates in a power consumption range of about 4 to 50 watts; and
a catalyst-free decomposing zone within said chamber proximate said outlet;
said chamber being arranged to move air from the inlet through the inactivating zone and the decomposing zone in a turbulent, non-straight line flow whereby the ozone concentration in the air expelled from said chamber is less than about 0.3 ppm.

15. A device as defined in claim 14 further including an electrostatic post filter arranged proximate said outlet to receive and treat air from said decomposing zone.

16. A device as defined in claim 15 wherein the ozone generator is of tubular construction and comprises a borosilicate glass dielectric with stainless steel gauge electrodes on opposite sides thereof.

* * * * *